(12) United States Patent
Kushwaha et al.

(10) Patent No.: US 10,426,880 B2
(45) Date of Patent: Oct. 1, 2019

(54) VENTRICULAR ASSIST DEVICE AND METHOD

(71) Applicant: MI-VAD, INC., Rochester, MN (US)

(72) Inventors: Sudhir Kushwaha, Rochester, MN (US); Zain Khalpey, West Roxbury, MA (US)

(73) Assignee: MI-VAD, INC., Rochester, MN (US)

( * ) Notice: Subject to any disclaimer, the term of this patent is extended or adjusted under 35 U.S.C. 154(b) by 0 days.

(21) Appl. No.: 15/121,708

(22) PCT Filed: Feb. 25, 2015

(86) PCT No.: PCT/US2015/017499
§ 371 (c)(1),
(2) Date: Aug. 25, 2016

(87) PCT Pub. No.: WO2015/130768
PCT Pub. Date: Sep. 3, 2015

(65) Prior Publication Data
US 2017/0216507 A1   Aug. 3, 2017

Related U.S. Application Data

(60) Provisional application No. 61/944,490, filed on Feb. 25, 2014.

(51) Int. Cl.
*A61M 1/12* (2006.01)
*A61M 1/10* (2006.01)
(Continued)

(52) U.S. Cl.
CPC .............. *A61M 1/125* (2014.02); *A61F 2/07* (2013.01); *A61F 2/82* (2013.01); *A61F 2/90* (2013.01);
(Continued)

(58) Field of Classification Search
CPC .............. A61M 1/1005; A61M 1/1015; A61M 1/1017; A61M 1/1024; A61M 1/1036; A61M 1/122
See application file for complete search history.

(56) References Cited

U.S. PATENT DOCUMENTS 4,382,199 A    5/1983   Isaacson
4,625,712 A   12/1986   Wampler
(Continued)

FOREIGN PATENT DOCUMENTS

| EP | 2338541 A1 | 6/2011 |
|----|------------|--------|
| EP | 2363157 A1 | 9/2011 |
| WO | WO-2008/024714 A1 | 2/2008 |

OTHER PUBLICATIONS

European Patent Office, European Extended Search Report and Search Opinion for European Application No. EP 15755879.2 dated Sep. 5, 2017.
(Continued)

*Primary Examiner* — Paula J Stice
(74) *Attorney, Agent, or Firm* — Marshall, Gerstein & Borun LLP

(57) ABSTRACT

A ventricular assist device includes a stent for placement within a cardiac artery and arranged for placement, the stent arranged to have an open configuration defining a flow path, a rotor sized to fit within the stent and arranged for percutaneous placement the flow path, the rotor including a surface disposed about a central portion and angled with respect to the flow path and having a first plurality of magnets. A collar is sized for placement about the cardiac artery and includes a stator. A power source is coupled to the stator, and the stator and the rotor are arranged to rotate the rotor about an axis. A timing control module controls a rotational speed of the rotor. Accordingly, the surface of the
(Continued)

rotor is arranged to move blood along the flow path in response to rotation of the rotor.

11 Claims, 18 Drawing Sheets

(51) Int. Cl.
*A61F 2/82* (2013.01)
*A61F 2/07* (2013.01)
*A61F 2/90* (2013.01)
*A61F 2/95* (2013.01)
A61F 2/06 (2013.01)

(52) U.S. Cl.
CPC .............. *A61F 2/95* (2013.01); *A61M 1/101* (2013.01); *A61M 1/1005* (2014.02); *A61M 1/1015* (2014.02); *A61M 1/1017* (2014.02); *A61M 1/1024* (2014.02); *A61M 1/1036* (2014.02); *A61M 1/1086* (2013.01); *A61M 1/122* (2014.02); *A61M 1/127* (2013.01); A61F 2002/068 (2013.01); A61F 2210/009 (2013.01); A61M 1/1001 (2014.02); A61M 1/1008 (2014.02); A61M 1/1013 (2014.02); A61M 1/1018 (2014.02); A61M 1/1031 (2014.02); A61M 2205/0238 (2013.01); A61M 2205/3365 (2013.01); A61M 2205/3507 (2013.01); A61M 2210/127 (2013.01); A61M 2230/04 (2013.01)

(56) References Cited

U.S. PATENT DOCUMENTS

| | | | |
|---|---|---|---|
| 4,753,221 A | 6/1988 | Kensey et al. | |
| 4,779,614 A | 10/1988 | Moise | |
| 4,817,586 A | 4/1989 | Wampler | |
| 4,908,012 A | 3/1990 | Moise et al. | |
| 4,919,647 A | 4/1990 | Nash | |
| 4,944,748 A | 7/1990 | Bramm et al. | |
| 4,957,504 A | 9/1990 | Chardack | |
| 4,994,017 A | 2/1991 | Yozu | |
| 4,995,857 A | 2/1991 | Arnold | |
| 5,049,134 A | 9/1991 | Golding et al. | |
| 5,078,741 A | 1/1992 | Bramm et al. | |
| 5,112,202 A | 5/1992 | Oshima et al. | |
| 5,290,227 A | 3/1994 | Pasque | |
| 5,326,344 A | 7/1994 | Bramm et al. | |
| 5,385,581 A | 1/1995 | Bramm et al. | |
| 5,507,629 A | 4/1996 | Jarvik | |
| 5,527,159 A | 6/1996 | Bozeman, Jr. et al. | |
| 5,613,935 A | 3/1997 | Jarvik | |
| 5,676,651 A | 10/1997 | Larson, Jr. et al. | |
| 5,678,306 A | 10/1997 | Bozeman, Jr. et al. | |
| 5,695,471 A | 12/1997 | Wampler | |
| 5,711,753 A | 1/1998 | Pacella et al. | |
| 5,722,930 A | 3/1998 | Larson, Jr. et al. | |
| 5,762,599 A | 6/1998 | Sohn | |
| 5,840,070 A | 11/1998 | Wampler | |
| 5,924,975 A | 7/1999 | Goldowsky | |
| 5,928,131 A | 7/1999 | Prem | |
| 5,941,813 A | 8/1999 | Sievers et al. | |
| 5,947,892 A | 9/1999 | Benkowski et al. | |
| 6,015,272 A | 1/2000 | Antaki et al. | |
| 6,080,133 A | 6/2000 | Wampler | |
| 6,135,943 A | 10/2000 | Yu et al. | |
| 6,179,773 B1 | 1/2001 | Prem et al. | |
| 6,200,260 B1 | 3/2001 | Bolling | |
| 6,201,329 B1 | 3/2001 | Chen | |
| 6,227,797 B1 | 5/2001 | Watterson et al. | |
| 6,234,998 B1 | 5/2001 | Wampler | |
| 6,244,835 B1 | 6/2001 | Antaki et al. | |
| 6,293,901 B1 | 9/2001 | Prem | |
| 6,363,276 B1 | 3/2002 | Prem et al. | |
| 6,368,083 B1 | 4/2002 | Wampler | |
| 6,375,607 B1 | 4/2002 | Prem | |
| 6,447,441 B1 | 9/2002 | Yu et al. | |
| 6,527,521 B2 | 3/2003 | Noda | |
| 6,609,883 B2 | 8/2003 | Woodard et al. | |
| 6,610,004 B2 | 8/2003 | Viole et al. | |
| 6,688,861 B2 | 2/2004 | Wampler | |
| 6,716,157 B2 | 4/2004 | Goldowsky | |
| 6,719,791 B1 | 4/2004 | Nusser et al. | |
| 6,761,532 B2 | 7/2004 | Capone et al. | |
| 6,817,836 B2 | 11/2004 | Nose et al. | |
| 6,979,351 B2 | 12/2005 | Forsell et al. | |
| 7,029,433 B2 | 4/2006 | Chang | |
| 7,125,376 B2 | 10/2006 | Viole et al. | |
| 7,229,258 B2 | 6/2007 | Wood et al. | |
| 7,238,151 B2 | 7/2007 | Frazier | |
| 7,284,956 B2 | 10/2007 | Nose et al. | |
| 7,331,921 B2 | 2/2008 | Viole et al. | |
| 7,462,019 B1 | 12/2008 | Allarie et al. | |
| 7,479,102 B2 | 1/2009 | Jarvik | |
| 7,699,586 B2 | 4/2010 | LaRose et al. | |
| 7,699,588 B2 | 4/2010 | Mendler | |
| 7,762,941 B2 | 7/2010 | Jarvik | |
| 7,850,594 B2 | 12/2010 | Sutton et al. | |
| 7,878,967 B1 | 2/2011 | Khanal | |
| 7,959,551 B2 | 6/2011 | Jarvik | |
| 7,998,054 B2 | 8/2011 | Bolling | |
| 7,998,190 B2 | 8/2011 | Gharib et al. | |
| 8,012,079 B2 | 9/2011 | Delgado, III | |
| 8,075,472 B2 | 12/2011 | Zilbershlag et al. | |
| 8,077,254 B2 | 12/2011 | Yu | |
| 8,088,059 B2 | 1/2012 | Jarvik | |
| 8,096,935 B2 | 1/2012 | Sutton et al. | |
| 8,177,703 B2 | 5/2012 | Smith et al. | |
| 8,353,686 B2 | 1/2013 | Cook | |
| 8,403,824 B2 | 3/2013 | Foster | |
| 8,409,276 B2 | 4/2013 | Wampler | |
| 8,419,609 B2 | 4/2013 | Shambaugh, Jr. et al. | |
| 9,067,006 B2 | 6/2015 | Toellner | |
| 9,107,992 B2 * | 8/2015 | Kushwaha | A61M 1/127 |
| 2001/0039369 A1 | 11/2001 | Terentiev | |
| 2003/0127090 A1 | 7/2003 | Gifford et al. | |
| 2003/0163020 A1 | 8/2003 | Frazier | |
| 2005/0085683 A1 | 4/2005 | Bolling et al. | |
| 2006/0030748 A1 | 2/2006 | Woodard et al. | |
| 2006/0036127 A1 | 2/2006 | Delgado | |
| 2007/0270633 A1 | 11/2007 | Cook et al. | |
| 2008/0200750 A1 | 8/2008 | James | |
| 2008/0269880 A1 | 10/2008 | Jarvik | |
| 2009/0069854 A1 | 3/2009 | Keidar et al. | |
| 2009/0112312 A1 | 4/2009 | LaRose et al. | |
| 2009/0118567 A1 | 5/2009 | Siess | |
| 2009/0204205 A1 | 8/2009 | LaRose et al. | |
| 2010/0069847 A1 | 3/2010 | LaRose et al. | |
| 2010/0076247 A1 | 3/2010 | Zilbershlag et al. | |
| 2010/0121438 A1 | 5/2010 | Jarvik | |
| 2010/0152524 A1 | 6/2010 | Sentmanat | |
| 2011/0144744 A1 | 6/2011 | Wampler | |
| 2011/0152999 A1 | 6/2011 | Hastings et al. | |
| 2011/0201870 A1 | 8/2011 | Forsell | |
| 2011/0301403 A1 | 12/2011 | LaRose et al. | |
| 2012/0294727 A1 | 11/2012 | Roehn | |
| 2013/0066139 A1 | 3/2013 | Wiessler et al. | |
| 2013/0138205 A1 | 5/2013 | Kushwaha et al. | |
| 2013/0281762 A1 | 10/2013 | Kushwaha et al. | |

OTHER PUBLICATIONS

International Search Report, corresponding to International Application No. PCT/US2015/017499, dated Jun. 3, 2015.
International Preliminary Report on Patentability and Written Opinion, corresponding to International Application No. PCT/US2015/017499, dated Aug. 30, 2016.
International Search Report and Written Opinion for International application No. PCT/US2012/066685, dated Mar. 5, 2013.
International Preliminary Report on Patentability and Written Opinion for International Application No. PCT/US2012/066685, dated Jun. 12, 2014.

(56) References Cited

OTHER PUBLICATIONS

K. Gu et al., "Development of Ventricular Assist Devices in China: Present Status, Opportunities and Challenges" European Journal of Cardio-Thoracic Surgery (2014), pp. 1-7, Published by Oxford University Press, Europe, Feb. 25, 2014.

* cited by examiner

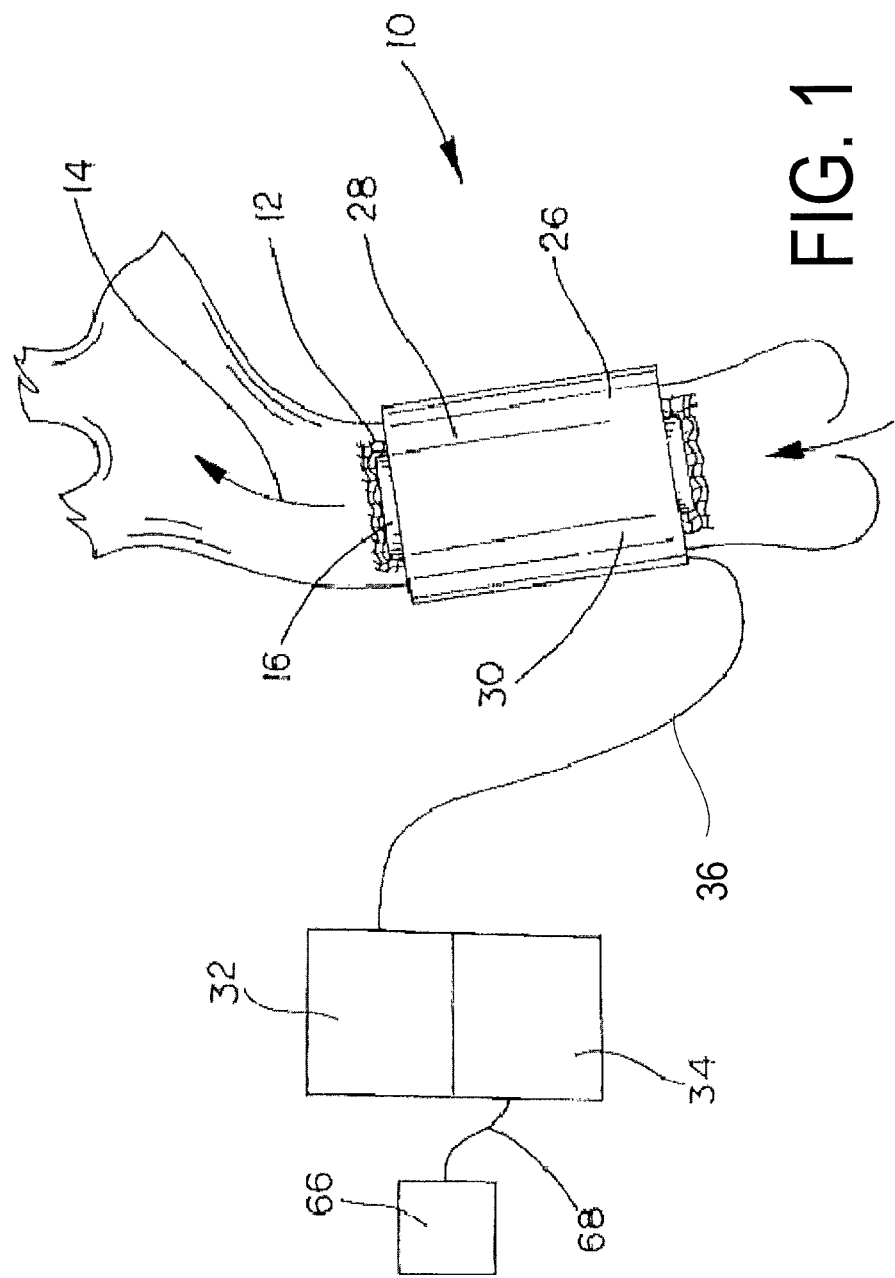

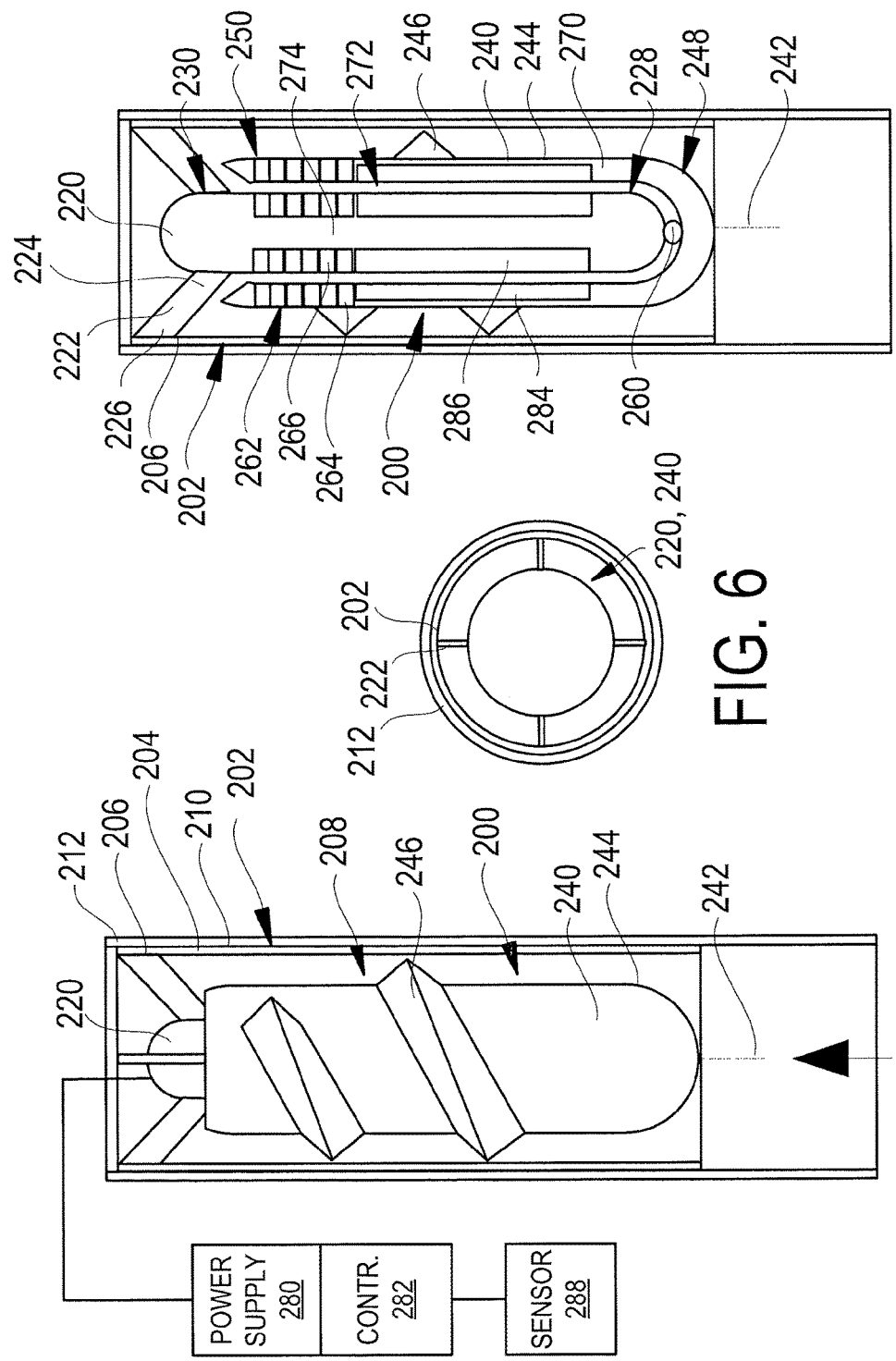

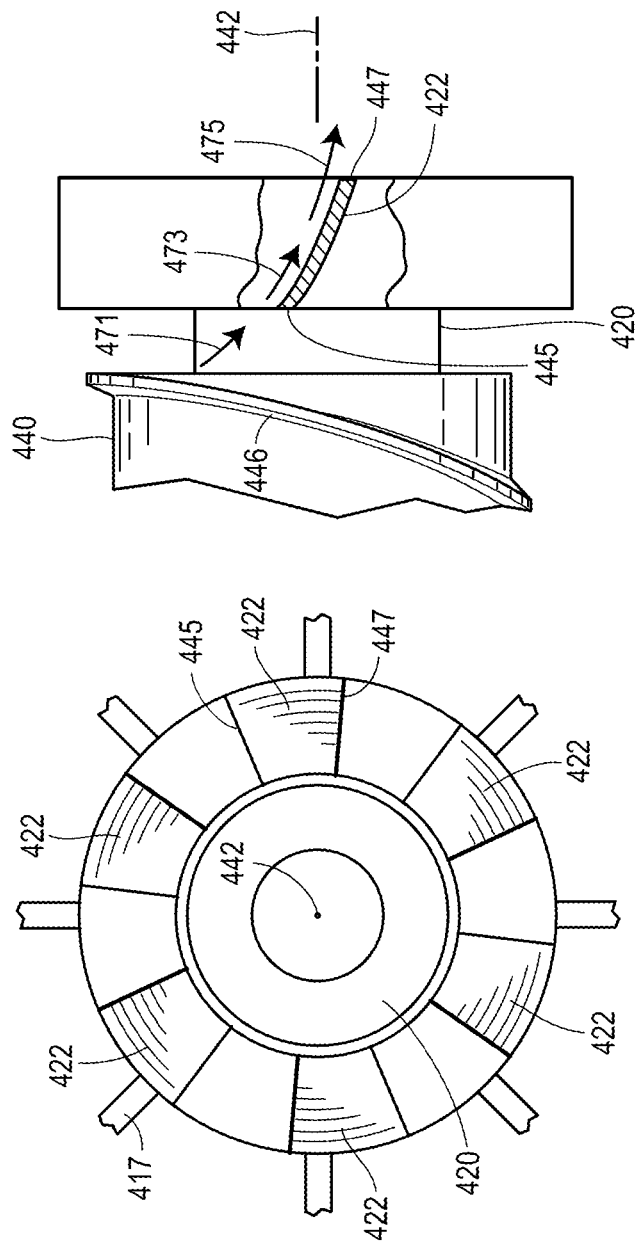

US 10,426,880 B2

VENTRICULAR ASSIST DEVICE AND METHOD

FIELD OF THE INVENTION

The present invention relates to a ventricular assist device and, more specifically, to a ventricular assist device suitable for assisting either the left ventricle, the right ventricle, or both ventricles.

BACKGROUND

Left ventricular assist devices are now a therapeutic option in patients with end-stage dilated cardiomyopathy. Existing device are designed for use in severe left ventricular failure. These existing devices have little adaptability for support of the right sided circulation and, in particular, are not well-suited for right ventricular failure. Current device designs also tend to be appropriate for patients with dilated cardiomyopathy, but these devices are not well-suited for use in patients with restrictive cardiomyopathy. Unfortunately, the outcome has been poor for past attempts to existing devices for restrictive cardiomyopathy.

Additionally, further problems with the present generation of devices include the risk of thrombus formation and the risk of infection, as well as negative effects of non-physiologic (non-pulsatile) flow. Non-physiologic flow can potentially cause a number of side-effects, including a high prevalence of gastrointestinal and/or cerebral bleeding. The etiology of the gastrointestinal bleeding is in part related to the non-physiologic flow, and may also be related to the depletion of clotting factors within the blood which may be destroyed by such a non-physiologic assist device. Some existing devices are known to have a 30% incidence of clotting factor depletion.

Current devices also may be difficult to use in the setting of an acute myocardial infarction. In such a situation, the freshly infarcted myocardial tissue may be friable, particularly if the location is apical or anterior. Consequently, use of existing devices may not be feasible because of the apical placement of the inflow cannula.

SUMMARY

In accordance with one aspect, a ventricular assist device for a human heart may comprise a stent sized for placement within a cardiac artery and arranged for percutaneous placement at a selected location within the cardiac artery, with the stent arranged to have an open configuration defining a flow path, a rotor sized to fit within the stent and arranged for percutaneous placement at the selected location and within the flow path, with the rotor including a surface disposed about a central portion and angled with respect to the flow path, the rotor further defining a longitudinal axis and having a first plurality of magnets. The device includes a collar sized for placement about the cardiac artery at the selected location, with the collar comprising a stator having an electrical winding. A power source is provided and is operatively coupled to the stator, and the stator and the rotor are arranged to interact in response to the application of power from the power source to the stator to cause the rotor to rotate about the longitudinal axis. A timing control module is provided and is operatively coupled to the stator, and is arranged to control a rotational speed of the rotor. Accordingly, the surface of the rotor is arranged to move blood along the flow path in response to rotation of the rotor.

In accordance with one or more preferred aspects, the collar includes a magnet set and the rotor includes a second plurality of magnets, the magnet set of the collar and the second plurality of magnets of the rotor cooperating to control a longitudinal position of the rotor with respect to the flow path. The selected location can be the aorta, which allows the device to function as a left ventricular assist device, or may be the pulmonary artery, which allows the device to function as a right ventricular assist device. Still further, the device may be placed in both the aorta and the pulmonary artery, which allows the device to function as a bi-ventricular assist device. Preferably, the selected location or locations may be supravalvular. Still further, the collar may be adapted for minimally invasive placement about the appropriate vessel or vessels.

The surface of the rotor may be formed by a plurality of blades, the surface of the rotor may be helical, the surface of the rotor may comprise a plurality of surfaces, and the surface of the rotor may comprise any suitable form or shape to permit movement of blood along the flow path in response to rotation of the rotor.

Preferably, the timing control module is operatively coupled to a sensor arranged to sense native cardiac rhythms, and the timing module is arranged to control the rotational speed of the rotor in response to the native cardiac rhythms. The timing control module may further be arranged to control the rotational speed of the rotor between a baseline speed and a higher speed, wherein the baseline speed is arranged to allow the device to function as a closed valve, and wherein the higher speed is arranged to move blood along the flow path at a desired flow rate.

Still preferably, one or both of the rotor and the stent are coated with an anti-coagulant. The power the power source may be subcutaneous, and may be arranged for transcutaneous charging.

In accordance with another aspect, a ventricular assist device for a human heart may comprise a stent sized for placement within a cardiac artery at a selected location within the cardiac artery and arranged to define a flow path, a magnetized rotor sized to fit within the stent and at the selected location and within the flow path, the rotor including a surface angled with respect to the flow path and including a longitudinal axis, and a collar. The collar is sized for placement about the cardiac artery at the selected location, with the collar comprising a stator having an electrical winding. The device includes a power source operatively coupled to the stator, and the stator and the rotor are arranged to interact in response to the application of power from the power source to the stator to cause the rotor to rotate about the longitudinal axis. A timing control module is provided, and the timing control module is operatively coupled to the stator and is arranged to control a rotational speed of the rotor between a baseline first speed and a higher second speed. The surface of the rotor is arranged to move blood along the flow path in response to rotation of the rotor.

In accordance with a further aspect, a ventricular assist device for a human heart includes a stent, a stator, a rotor, a power source, and a controller. The stent has a cylindrical stent wall with an inner surface defining a flow path and an outer surface configured to be disposed within a blood vessel. The stator is disposable within the stent, the stator having a plurality of support struts connected to the stator and disposable against the inner surface of the stent wall to position the stator within the stent. The rotor includes an outer surface facing the inner surface of the stent wall and defined in part by at least one blade angled with respect to the flow path, the rotor rotatably mounted on the stator between the inner surface of the stent and the stator. One of the rotor and the stator includes a field magnet and the other of the rotor and the stator includes windings. The power source is operatively coupled to the windings, and the controller is operatively coupled to the power source to selectively control the power source to vary the speed of the rotor.

It will be recognized that any of the aspects may be combined with or modified in light of the preferred aspects disclosed herein, as desired.

When assembled in accordance with one or more preferred forms outlined herein, the device may be placed using a minimally invasive, off-pump approach. Epi-aortic magnets may be placed around the ascending aorta or other desired location, while the magnetically suspended (or levitated) rotor or impeller blade is placed in a supravalvular position, above the aortic valve or the pulmonary valve, thus permitting use in either severe left ventricular failure of severe right ventricular failure. Known devices appear unsuitable for placement at one or more of these locations.

By placing the device using a minimally invasive approach in a supravalvular position, the anatomic integrity of the left ventricle or the right ventricle may not be affected, and there is a lower risk of complications related to disruption of the integrity of the ventricular architecture. This may be particularly beneficial in patients experiencing cardiogenic shock following acute myocardial infarction, or experiencing biventricular failure requiring off-pump support to off-load the ventricle(s).

A rotor or impeller blade may be levitated within the stent. Both may be deployed separately and sequentially through the groin using standard techniques with existing methods. The in-stent rotor or impeller may be mounted within the ascending aortic or pulmonary arteries, to support the left or right ventricles respectively. The levitation of the rotor or impeller prevents "touch-down" of the blade or blood driving surface against the wall of the surrounding vessel.

The placement and function of the disclosed device preferably allows the maintenance of pulsatile physiologic flow to augment the natural cardiac cycle of the heart. Preferably, the device achieves phasic blood flow through the use of electrical signals to time the pumping action via the timing control module to augment normal myocardial contractility. Power may be provided by a pacemaker type power unit implanted subcutaneously. In one preferred form, the device uses a transcutaneous charging system. Additionally, near field communication (NFC) technology could be used to impart instructions to the timing control module.

The device may function as an aortic or pulmonary valve. The disclosed device could be considered in place of a mechanical valve in circumstances where there are problems with the native aortic or pulmonary valves when associated with severe cardiac failure of the left or right ventricles respectively. For instance, in severe aortic stenosis with cardiac failure, the native diseased valve could be removed at the time of surgery and the device would—in effect— function as a valve. The same would be true with aortic regurgitation or infective endocarditis. On the right side of circulation, the device could be used in lieu of a pulmonary valve.

The device may assist in the prevention of thrombus or blood clots at the site of device implantation and within the device mechanism with the use of certain techniques. This could be accomplished by the use of systemic anticoagulation or the use of special coatings (e.g. fibrinogen like peptide 2), which prevent formation of thrombus on surfaces of the rotor and stent in contact with the blood. These features and uses are enumerated and discussed in more detail below.

Another aspect of the disclosed device would be the control of power and settings using a near field communication system to control the power requirements and output, the timing, and/or other settings. Such an approach may employ wireless cell phone technology, or other suitable technology, as a means of communication with the control unit. Thus the control system would not need any sort of cable or wired connection, and programming may be accomplished with hand-held devices, such as through a cell phone or other module. The device and its control system would be completely implantable.

BRIEF DESCRIPTION OF THE DRAWINGS

FIG. 1 is an elevational schematic view of a particular assist device assembled in accordance with the teachings of the present invention.

FIG. 5 is an enlarged fragmentary elevational view, partly in section, illustrating another exemplary form for a rotor, stator, and stent forming a portion of another assist device assembled in accordance with the teaching of the present invention.

FIG. 6 is an end view of the device of FIG. 5 with the fins of the rotor removed to better visualize supports connecting the stator to the stent.

FIG. 7 is a further enlarged fragmentary elevational view, in section, of the rotor, stator, and stent of FIG. 5.

FIG. 22 is a fragmentary left or downstream side elevational view of the assist device taken along line 22-22 of FIG. 20.

FIG. 23 is a fragmentary elevational view, partly in section, illustrating an exemplary form for the support struts disposed between the stator and the adjacent housing.

DETAILED DESCRIPTION OF THE INVENTION

Figure 3:
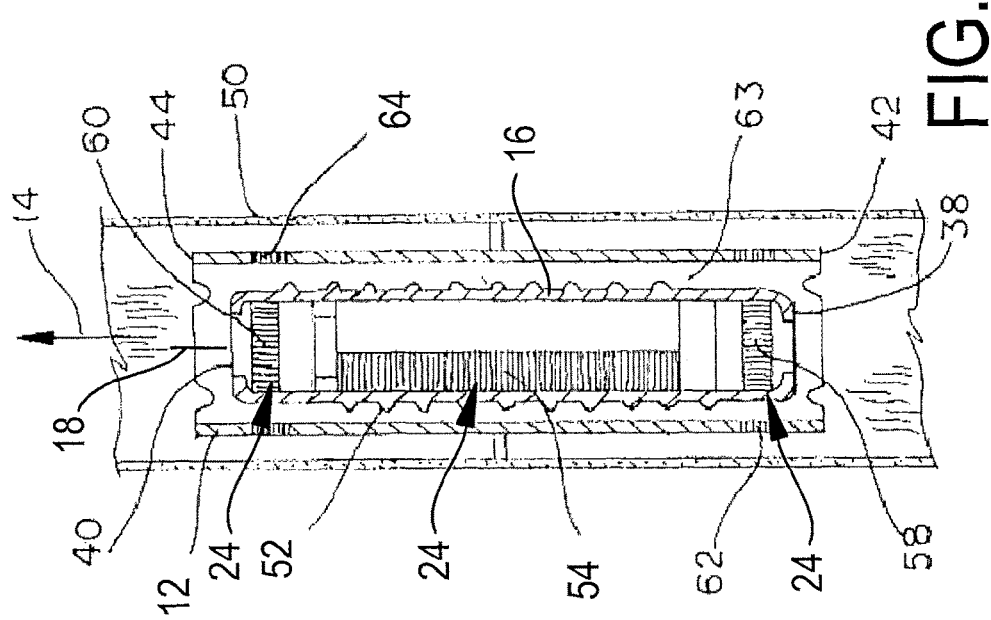
FIG. 3 is another enlarged fragmentary elevational view, partly in section, and similar to FIG. 2, but illustrating a plurality of magnets carried by cooperating portions of the stent and the rotor to control a longitudinal position of the rotor relative to the stent and/or the flow path.

Referring now to the drawings, FIG. 1 illustrates a ventricular assist device assembled in accordance with the teachings of a disclosed example of the present invention and referred to by the reference numeral 10. The device 10 is suitable for use at a selected location within the heart, which may be within either of two different cardiac arteries, as we explained in greater detail below. The device 10 includes a stent 12 (partially obscured in FIG. 1 but illustrated in greater detail at least in FIGS. 2 and 3). Preferably, stent 12 defines an axis 13 (see FIG. 2) and is sized for placement/to fit within the selected cardiac artery which may be, for example, the aorta or the pulmonary artery. By way of example, the diameter of the aorta and the pulmonary artery may be approximately 2.0 to 3.0 cm, with the diameter of each varying from individual to individual and even varying for the individual over the life of the individual, for example. The stent 12 preferably is arranged for percutaneous placement at the selected location within the cardiac artery, and is arranged to have an open configuration as shown in FIG. 1 in order to define a flow path 14 extending through the stent 12 and hence through the device 10. The device 10 also includes a rotor 16, which also is partially obscured in FIG. 1, but which is illustrated in greater detail at least in FIGS. 2 and 3.

Figure 2:
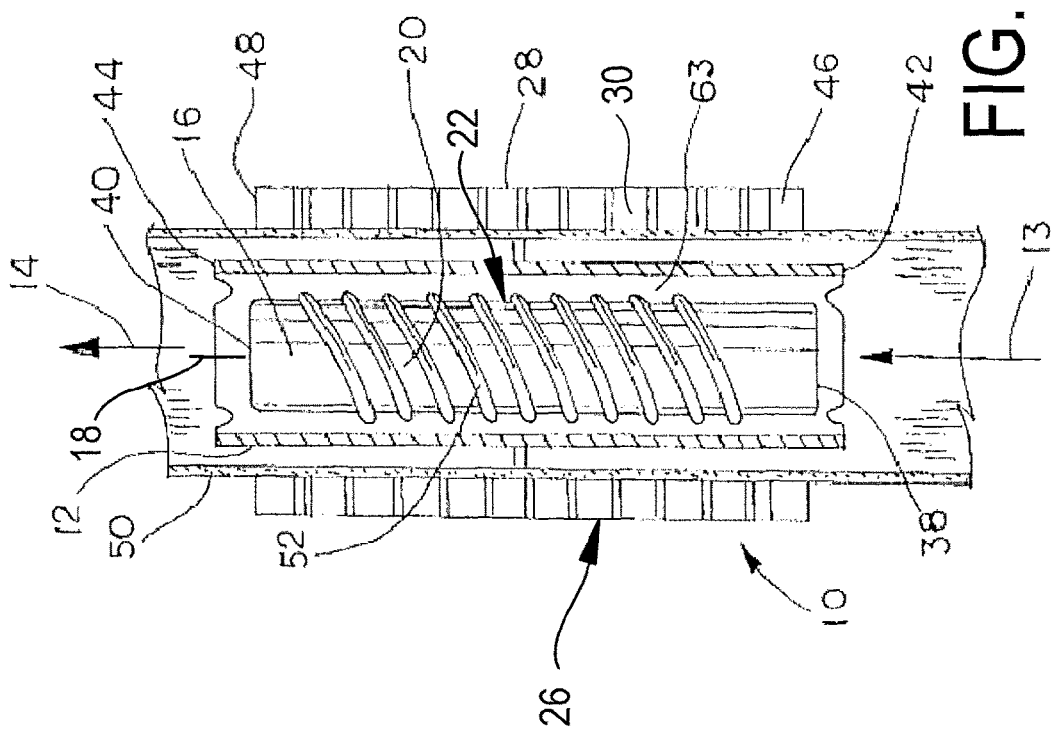
FIG. 2 is an enlarged fragmentary elevational view, partly in section, illustrating the rotor, stent, and the collar assembly forming a portion of the device illustrated in FIG. 1.

Referring still to FIG. 1, the rotor 16 also sized to fit within the selected cardiac artery and is also sized to fit within stent 12 and disposed within the flow path 14. Still preferably, the rotor 16 is arranged for percutaneous placement at the selected location within the cardiac artery. Referring now to FIG. 2, the rotor 16 generally defined a longitudinal axis 18, and fits within the stent 12 in such a fashion that the rotor 16 can rotate about its axis 18 as will be described in greater detail below. The rotor 16 further includes a surface 20 surrounding a central portion 22, with the surface 20 preferably angled relative to both the axis 18 and the central portion 22. The rotor 16 also includes a plurality of magnets 24 (the magnets are obscured in FIGS. 1 and 2, but are shown in greater detail in FIG. 3).

The device 10 also includes a collar 26 is sized for placement around the selected cardiac artery. As seen in FIGS. 1 and 2, the collar 26 includes a stator 28 having one or more suitable electrical windings 30. Referring to FIG. 1, the device 10 further includes a power source 32 and a timing control module 34, both of which are operatively coupled to the stator 28 (and in particular, the windings 30) via a suitable link 36. In response to the application of electrical power from the power source 32 to the stator 28 (windings 30), the stator 28 and certain of the magnets 24 on the rotor 16 interact, therefore causing the rotor to rotate about its axis 18 within the stent 12. Consequently, by virtue of the surface 20 on the rotor 16, the rotor 16 moves blood along the flow path 14.

Referring now to FIG. 2, the rotor 16 is shown disposed within the flow path 14 of the stent 12. The rotor 16 includes a first end 38 and a second end 40, while the stent 12 includes a first end 42 and a second end 44. The stator 28 also includes a first end 46 and a second end 48. As will be explained in greater detail below with respect to FIG. 3, the rotor 16 is suspended, levitated, or otherwise magnetically held in position or suspended inside the stent 12. The stent 12 is shown disposed immediately inside an arterial wall 50 which, as alluded to above, may be the wall of either the pulmonary artery or the aorta. The collar 26 (and hence the stator 28 and the winding 30) is disposed immediately outside the arterial wall 50. In the example of FIG. 2, the surface 20 is a helical surface 52 in which helical flighting extends outwardly from the central portion 22, generally between the first and 38 and the second end 40 of the rotor 16. As an alternative to the helical surface 52 shown in FIG. 2, the surface 20 of the rotor 16 may be carried by one or more blades. Preferably, the blades would be collapsible and therefore suitable for percutaneous delivery.

Referring now to FIG. 3, the magnets 24 of the rotor 16 are shown in greater detail. The magnets 24 include a first plurality of magnets 54 which are disposed around the rotor 16 so as to permit the first plurality of magnets 54 to interact with the stator 28 (and in particular the windings 30) to rotate the rotor 16 about its axis 18 in response to the application of power as outlined above. The magnets 24 also include a second plurality of magnets, including one or more magnets 58 disposed adjacent the first end 38 of the rotor 16, and one or more magnets 60 disposed adjacent the second end 40 of the rotor 16. In the example of FIG. 3, the stent 12 also includes one or more magnets 62 disposed adjacent the first end 42 of the stent 12, and one or more magnets 64 disposed adjacent the second end 44 of the stent 12. The magnets 58, 60 may be ring-shaped so as to extend generally around the axis 18 of the rotor 16. Similarly, the magnets 62, 64 also being ring-shaped so as to extend generally around the axis 13 of the stent 12. The magnets 58, 60, 62 and 64 interact to maintain the longitudinal position of the rotor 16 within the stent 12, so as to prevent the rotor from undesired movement along its axis 18 and along the flow path 14. The magnets 58, 60 may be disposed on an outer surface of the rotor 16, may be disposed under the outer surface of the rotor 16, or may be disposed in any other suitable fashion. Similarly, the magnets 62 and 64 may be disposed on an inner surface, an outer surface, between the inner and outer surfaces of the stent 12, or in any other suitable fashion. Preferably, the rotor 12 is levitated or suspended as explained above in such a fashion that the outer-most extremities of the rotor 12 are separated from the inner surface of the stent 12 by a gap 63.

Referring once again to FIG. 1, the device 10 preferably includes a sensor 66 which is arranged to sense native cardiac rhythms. The sensor 66 is operatively coupled to the timing control module 34 by a suitable link 68. Consequently, the timing of the pumping action may be arranged to work in conjunction with the native cardiac rhythms. In one preferred form, the timing control module 34 is arranged to control the rotational speed of the rotor between a baseline speed and a higher speed. The baseline speed may be zero, or non-zero. There may be power-saving advantages to maintaining the baseline speed as a non-zero speed. When the rotor 16 is at or near the baseline speed, the rotor 16 may effectively function as a closed valve. On the other hand, at the higher speed the rotor 16 is arranged to move blood along the flow path at a desired flow rate. Still preferably, one or both of the rotor 16 and the stent 12 may be coated with an anti-coagulant. Further, the power source 32, the timing control module 34, and the sensor 66 all are preferably subcutaneous. Still preferably, the power source may be arranged for transcutaneous charging.

As another alternative, the timing control module 34 may be programmed or otherwise arranged to control the rotational speed of the rotor to create a first flow characteristic and a second flow characteristic. For example, the control of the rotor may be such that the first flow characteristic creates at least a partial reverse flow, which would be opposite the direction of the flow path 14. In accordance with at least one exemplary form, such a flow characteristic may act to improve coronary perfusion. The control of the rotor further may be such that the second flow characteristic creates a forward flow, which is along, or otherwise in the direction of, the flow path 14. Preferably, by using the sensor 66, the rotation of the rotor may be gated with the native cardiac rhythms, which allows the device 10 to behave in a manner similar to the behavior of an intra-aortic balloon pump (IABP), with positive forward flow as well as at least some reverse flow.

Figure 4:
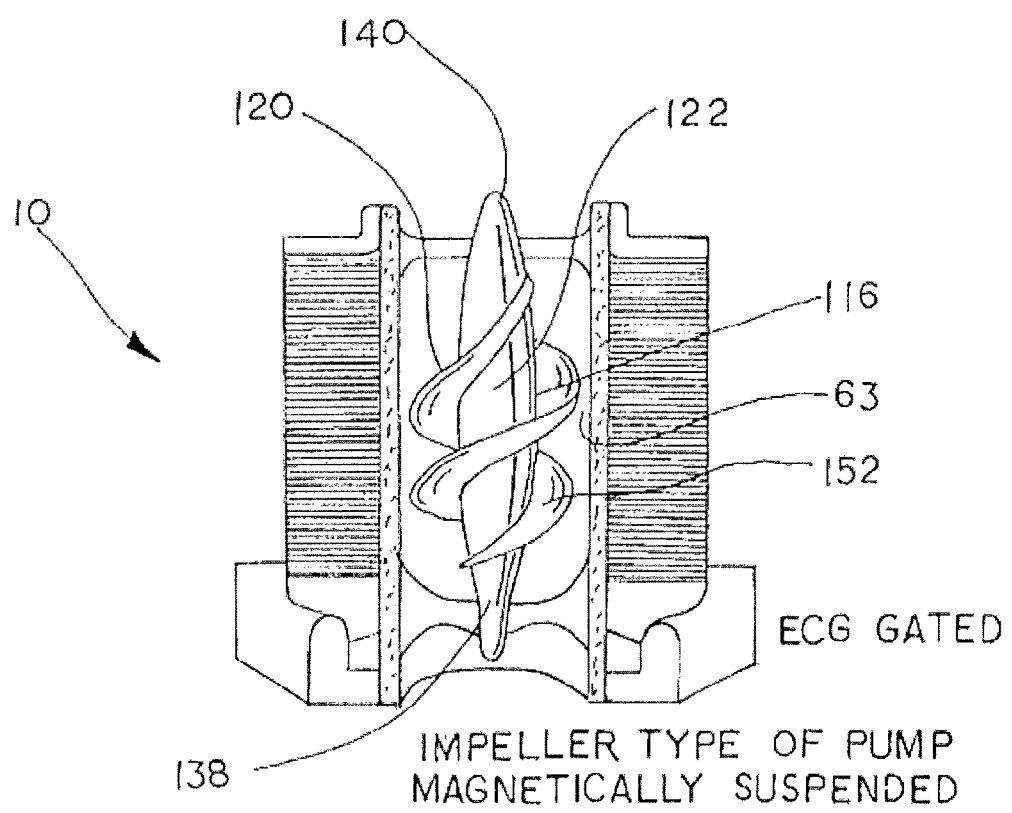
FIG. 4 is an enlarged cross-sectional view of similar to FIG. 2 but illustrating another exemplary form for the rotor, stent, and collar assembly.

FIG. 4 illustrates an alternative rotor 116. The rotor 116 may be similar in most respects to the rotor 16 discussed above, and may be suspended and rotated as discussed above. Thus, like components need not be discussed in further detail. The rotor 116 includes a central portion 122 that is wider in the middle and tapers toward each end 138 and 140. A surface 120 of the rotor 116 includes a helical surface 152, and the helical surface 152 or flighting again extends radially outwardly from the central portion 122. In the example of FIG. 4, the helical surface extends outwardly from the central portion 122 a first distance adjacent a middle portion of the rotor 116, and extends a second and lesser distance adjacent the ends 138, 140. As with the example discussed above, the gap 63 is formed between an outer extent of the flighting or blades, and an inner surface of the surrounding stent. Further, preferably the surface that drives the blood flow (the helical flighting, blades, or other suitably shaped surface or structure) would be collapsible and therefore suitable for percutaneous delivery. One of skill in the art, upon reading the present disclosure, will understand that features of the rotor 16 and the rotor 116 need not be mutually exclusive. Instead, one may combine and/or substitute aspects of the two rotors as desired.

FIGS. 5-7 illustrate another embodiment of a ventricular assist device assembled in accordance with the teachings of a disclosed example of the present invention. The device 200, like the devices 10 discussed in relation to FIGS. 1-4, is suitable for use and sized for placement/to fit at a selected location (e.g., supravalvular) within the heart, which may be either of two different cardiac arteries, or elsewhere in the vasculature. The device 200 includes a stent 202 with a cylindrical stent wall 204 with an inner surface 206 defining a flow path 208 extending through the stent 202 (and hence through the device 200) and an outer surface 210 configured to be disposed within a blood vessel 212, such as a cardiac artery, as mentioned previously. The stent 202 (and in particular the wall 204) may be defined by a metal (e.g. titanium) or other suitable material mesh tube, as is conventionally known.

Referring to FIG. 5, the device 200 also includes a stator 220. Unlike the stator 28 mentioned relative to the device 10, the stator 220 of the device 200 is disposable in (and, as illustrated in FIGS. 5-7, is disposed in) the stent 202. As illustrated in FIG. 7, the stator 220 has a plurality of support struts 222 each having a first end 224 connected to the stator 220 and a second end 226 disposable against the inner surface 206 of the stent 202 (and in particular the stent wall 204) to position the stator 220 within the stent 202. Further, as illustrated in FIG. 7, the stator 220 has an upstream end 228 and a downstream end 230, and the plurality of support struts 222 depend from the downstream end 230 of the stator 220. Additionally, as seen best in FIG. 6, the stator 220 may include four support struts 222 disposed equidistant about the stator 220. However, the number of struts 222 and their disposition along and about the stator 220 is for illustrative purposes only, and not by way of limitation. According to still further embodiments, the second end 226 may be configured to be securely connected to the inner surface 206 of the stent 202.

Returning to FIG. 5, the device further includes a rotor 240. Similar to the rotor 16, the rotor 240 is sized for placement/to fit within the stent 202 (and hence at the selected location) in such a fashion that the rotor 240 can rotate about its axis 242 within the flow path 208. Also similar to the rotor 16, the rotor 240 has an outer surface 244 facing the inner surface 206 of the stent wall 204 and is defined in part by at least one blade (or flighting) 246 angled with respect to the flow path 208. In this regard, it may also be possible to refer to the blade 246 as angled relative to the axis 242 of the rotor 240 as well. The rotor 240 has an upstream end 248 and a downstream end 250 (see FIG. 7), and the blade or flighting 246 may be formed on the outer surface 244 of the rotor 240 between the upstream and downstream ends 248, 250, but may or may not cover the entire outer surface 244 of the rotor 240 between the upstream and downstream ends 248, 250.

The blade or flighting 246 may be collapsible against the outer surface 244 of the rotor 240. In particular, the blade 246 may be collapsible to facilitate delivery to the location of the stent 202. For example, as explained below, the device 200 may include an introducer jacket, and the blade(s) 246 may be collapsed against the rotor 240 (an in particular the outer surface 244) with the jacket disposed about the rotor 240. The blades 246 may extend from the outer surface 244 of the rotor 240 without the jacket disposed about the rotor 240 as is illustrated in FIGS. 5 and 7.

Unlike the embodiments in FIGS. 1-4, the rotor 240 is not received within the stator 220. Instead, the rotor 240 is rotatably mounted on the stator 220 between the inner surface 206 of the stent wall 204 (or stent 202) and the stator 220 as illustrated in FIG. 7. For example, the device 200 may include first and second bearings 260, 262 disposed between the stator 220 and rotor 240 to rotatably mount the rotor 240 on the stator 220. The first bearing 260 may be disposed at the upstream ends 228, 248 of the stator 220 and the rotor 240, while the second bearing 262 may be disposed at the downstream ends 230, 250 of the stator 220 and the rotor 240.

According to a first embodiment, the first bearing 260 may be a mechanical pivot. Alternatively, the first bearing 260 may be a hydrodynamic pivot. Further, the first bearing 260 may be a magnetic bearing, such as is described above relative to the embodiments of FIGS. 1-4 or below relative to bearing 262. Still other alternatives are possible according to the teachings of the disclosed example of the present invention.

Similarly, the second bearing 262 may take on various forms. As illustrated in FIG. 7, the second bearing 262 may be a magnetic bearing. In this regard, the bearing 262 may include first magnets 264 attached to the rotor 240 and second magnets 266 attached to the stator 220, the first magnets 264 and the second magnets 266 having aligned polarities such that the repulsion between the magnets 264, 266 will suspend the downstream end 250 of the rotor 240 from and about the downstream end 230 of the stator 220. In this regard, the embodiment illustrated in FIGS. 5-7 is similar to that illustrated in FIGS. 1-4, and in particular as explained relative to FIG. 3. For example, as explained relative to the magnets 58, 60, 62, 64, the magnets 264, 266 may be ring-shaped so as to extend generally around the axis 242 of the rotor 240 (and the axis of the stator 220 as well). Moreover, the magnets 264, 266 may be disposed on, in or under a surface of the rotor 240 or stator 220, or in any other suitable fashion. Further magnets may also be included to limit the axial motion of the rotor 240 relative to the stator 220 if, for example, a hydrodynamic or magnetic bearing is used as bearing 260.

As illustrated in FIG. 7, the rotor 240 may be rotatably mounted on the stator 220 by providing, in addition to the bearings 260, 262, a rotor 240 with an elongate, hollow body 270 that defines an enclosed space 272. The stator 220 may also have an elongate body 274 that is disposed or received at least partially (almost entirely, as illustrated) within the enclosed space 272 of the rotor 240. It will be recognized that this is merely one example, and not intended to be limiting.

As for the mechanism used to rotate the rotor 240, one of the rotor 240 and the stator 220 includes a field magnet and the other of the rotor 240 and the stator 220 includes coils or windings. As illustrated in FIG. 5, a power source 280 (similar to the power source 32 illustrated in FIG. 1) may be operatively coupled to the windings, and a controller 282 (similar to the timing control module 34 also illustrated in FIG. 1) may be operatively coupled to the power source 280. The controller 282 (which may include a processor and associated memory and/or circuitry and may be programmed/assembled to control the power source 280) selectively controls the power source 280 to vary the speed of the rotor 240.

In particular, referring to FIG. 7, the rotor 240 includes a field magnet 284, which may be in the form of a permanent magnet, similar to the magnets 54 of the embodiment illustrated in FIGS. 1-4. Further, the stator 220 includes windings 286, which may be in the form of windings or coils (e.g., copper coils), similar to the windings 30 of the embodiment illustrated in FIGS. 1-4. In response to the application of electrical power from the power source 280, to the windings 286, the windings 286 interact with the magnet 284, causing the rotor 240 to rotate about its axis 242 within the stent 202. Consequently, by virtue of the blade 246 on the rotor 240, the rotor 240 moves blood along the flow path 208.

Figure 19:
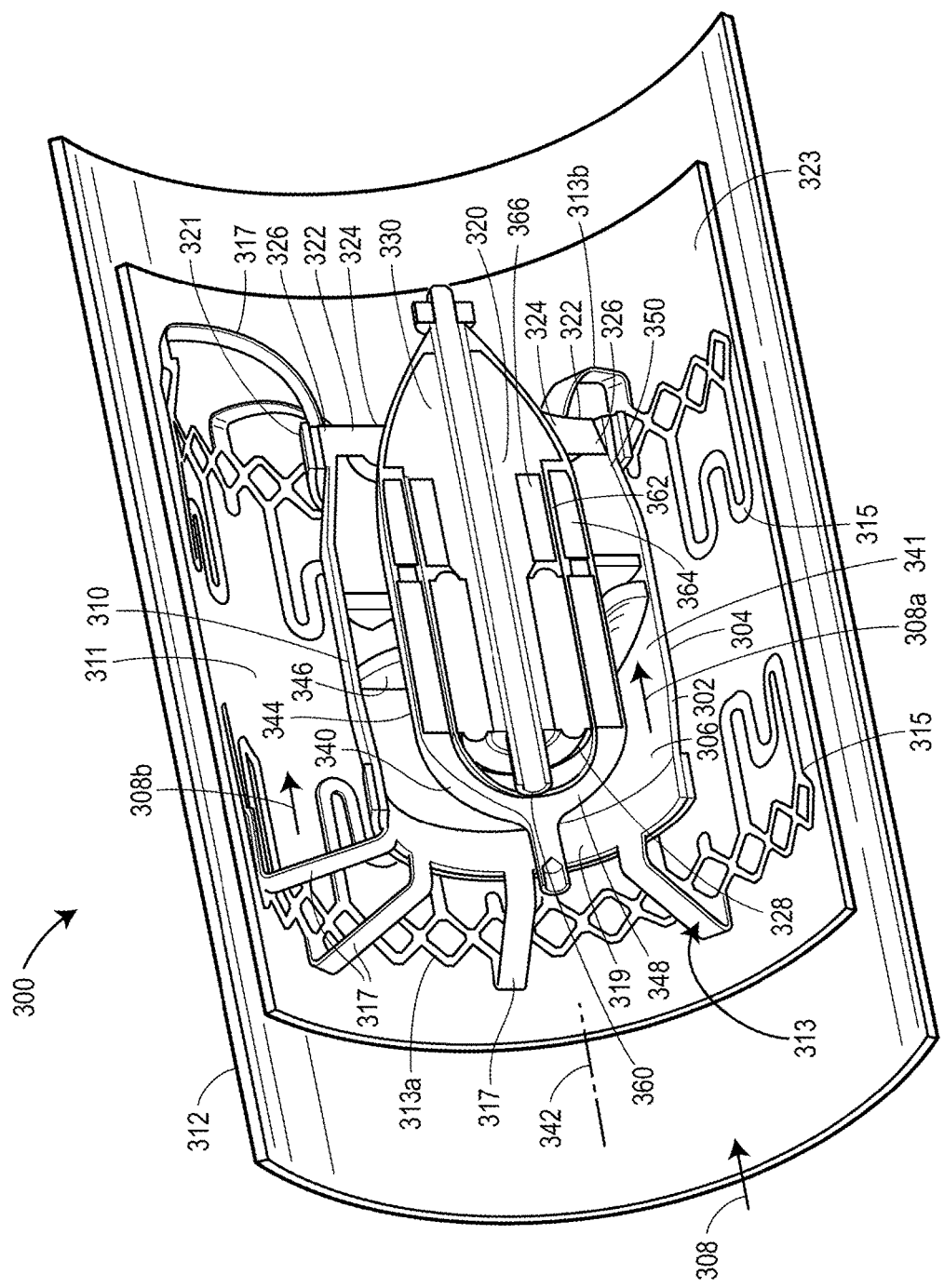
FIG. 19 is an enlarged perspective view, partly in section, illustrating still another exemplary form for an assist device including a rotor and stator disposed within a housing and assembled in accordance with the teaching of the present invention.

FIG. 19 illustrates another exemplary embodiment for a ventricular assist device 300 assembled in accordance with the teachings of a further disclosed example of the present invention. The device 300, like the devices 10 and 200 discussed in relation to FIGS. 1-4 and FIGS. 5-7 above, is again suitable for use and sized for placement/to fit at a selected location (e.g., supravalvular) within the heart, which may be either of two different cardiac arteries. As with the embodiments discussed above, the device 300 may also prove suitable for use elsewhere in the vasculature. The device 300 includes a shroud or flow housing 302. For purposes of the following discussion, the term flow housing will be used. The flow housing 302 includes a cylindrical wall 304 with an inner surface 306 and an outer surface 310. The flow housing 302 is sized and configured to be disposed within a blood vessel 312, such as a cardiac artery, as mentioned previously. In the example shown, the flow housing is sized to define an annular space 311 between the outer surface 310 of the flow housing 302 and the surrounding blood vessel 312.

In the example shown, the flow housing 302 is supported and/or otherwise secured in place within the blood vessel 312 by a support assembly 313, which operatively couples the flow housing 302 to the surrounding blood vessel 312. As shown, the support assembly 313 includes one or more landing area portions 315 arranged to make contact with the surrounding blood vessel 312, and a plurality of connectors 317 that connect the flow housing 302 to the landing area portions 315. In the example shown, the support assembly 313 includes an upstream or first portion 313a which attaches to the flow housing 302 generally adjacent to a forward portion 319 of the flow housing 302, and further includes a downstream or second portion 313b which attaches to the flow housing 302 generally adjacent to a rearward portion 321 of the flow housing 302. Still other arrangements for supporting the flow housing 302 within the blood vessel 312 may prove suitable. The support assembly 313 may be pre-formed at a desired size, or may be expanded in place using conventional materials and methods.

As shown in FIG. 19, the landing areas 315 of the support assembly 313 may be suitably secured to the blood vessel 312 using any suitable means. Alternatively, the landing areas 315 of the support assembly 313 may be suitably secured to a vascular graft 323, which may be a Dacron or PTFE graft, or any other suitable vascular graft. With the use of the vascular graft 323, the device 300 may be placed as a unit at the desired location in the blood vessel 312 using any suitable delivery technique, such as a trans-apical approach. In turn, the vascular graft 323 may be suitably secured to the surrounding blood vessel 312 using conventional techniques. For example, the graft may be sutured to the surrounding vessel, the graft may be secured using conventional stent securing techniques, or magnetic securement such as magnetic rings. Still other means may prove suitable.

Referring still to FIG. 19, the device 300 also includes a stator 320. As with the stator 220 mentioned relative to the device 200, the stator 320 of the device 300 is disposed inside of the flow housing 302. As with the device of FIG.

7, the stator 320 has a plurality of support struts 322 each having a first end 324 connected to the stator 320 and a second end 326 disposed against the inner surface 306 of the flow housing 302 (and in particular the stent wall 304) to position the stator 320 within the flow housing 302. As with the device of FIGS. 5-7, the stator 320 has an upstream end 328 and a downstream end 330, and the plurality of support struts 322 depend from the downstream end 330 of the stator 320. Although only two (2) support struts 322 are visible in FIG. 19, additional support struts may be provided, such as the number of support struts visible in, for example, FIG. 22 discussed below. In the arrangements shown, the support struts 322 are preferably disposed equidistant about the stator 320. However, the number of struts 322 and their disposition along and about the stator 320 is for illustrative purposes only, and not by way of limitation. According to still further embodiments, the second end 326 may be configured to be securely connected to the inner surface 306 of the flow housing 302 using any other suitable means.

Referring still to FIG. 19, the device 300 further includes a rotor 340. The rotor 340 may be similar in many respects to the rotors outlined above with respect to the embodiment of FIGS. 5-7. Again, the rotor 340 is sized for placement within the flow housing 302 in such a fashion that the rotor 340 can rotate about its axis 342. In the example shown, the flow housing 302 and the rotor 340 are sized to define an annular space 341 between the rotor 340 and the inner surface 306 of the flow housing 302. Consequently, the device 300 defines a flow path 308 extending generally through the device 300. In the example shown, a first portion 308a of the flow path 308 extends through the flow housing 302 via the annular space 341 between the rotor 340 and the flow housing 302, and a second portion 308b of the flow path 308 extends around the flow housing 302 via the annular space 311 between the flow housing 302 and the surrounding blood vessel 312.

The rotor 340 has an outer surface 344 facing the inner surface 306 of the wall 304 of the flow housing 302, and the rotor 340 includes at least one blade (or other suitable flighting) 346, with the blade 346 angled with respect to the flow path 308. In this regard, it may also be possible to refer to the blade 346 as angled relative to the axis 342 of the rotor 340 as well. The rotor 340 has an upstream end 348 and a downstream end 350, and the blade 346 such as flighting may be formed on the outer surface 344 of the rotor 340 between the upstream and downstream ends 348, 350. The blade 346 may or may not cover the entire outer surface 344 of the rotor 340 between the upstream and downstream ends 348, 350. Preferably, an outer end of the blade 346 is spaced slightly from the inner surface 306 of the flow housing, leaving a small gap. The gap is best visible with respect to the embodiment of FIGS. 20-26 and will be discussed in greater detail below.

In the example of FIG. 19, the blades or blade 346 may be fixed, although in other forms the blades or blade 346 may be collapsible against the outer surface 344 of the rotor 340. In the example of FIG. 19, the device 300 is preferably delivered to the selected location within the blood vessel 312 with the rotor 340 already disposed within the flow housing 302, and thus it may not be necessary to have a collapsible blade or blades. However, as outlined above, the support assembly 313 may be collapsible or at least partially collapsible, and then expanded in place using conventional mechanisms.

The rotor 340 is rotatably mounted to the stator 320 using first and second bearings 360 and 362, which may be the same or similar to the bearings 260 and 262 discussed above with respect to the embodiment of FIGS. 5-7. As with the prior embodiment, the first bearing 360 may be a mechanical pivot. Alternatively, the first bearing 360 may be a hydrodynamic pivot. Further, the first bearing 360 may be a magnetic bearing, such as is described above relative to the prior embodiments. Still other alternatives are possible according to the teachings of the disclosed example of the present invention.

Similarly, the second bearing 362 may take on various forms. As illustrated in FIG. 7 with respect to the above-described example, the second bearing 362 may be a magnetic bearing. In this regard, the bearing 362 may include first magnets 364 attached to the rotor 340 and second magnets 366 attached to the stator 320, the first magnets 364 and the second magnets 366 having aligned polarities such that the repulsion between the magnets 364, 366 will suspend the downstream end 350 of the rotor 340 from and about the downstream end 330 of the stator 320. In this regard, the embodiment illustrated in FIG. 19 is similar to that illustrated in the above-described embodiments. As with the above-described examples, the rotor 340 includes a field magnet, which may be in the form of a permanent magnet, similar to the magnets discussed above in the embodiments of FIGS. 1-4 and 5-7. Further, the stator 320 includes windings, which may be in the form of windings or coils (e.g., copper coils), similar to the windings discussed above with respect to the prior embodiments. In response to the application of electrical power from the power source to the windings, the windings interact with the magnet, causing the rotor 340 to rotate about its axis 342 within the flow housing 302. Consequently, by virtue of the blades or blade 346 on the rotor 340, the rotor 340 moves blood along the flow path 308.

FIGS. 20-26 illustrate another exemplary embodiment for a ventricular assist device 400 assembled in accordance with the teachings of a further disclosed example of the present invention. The device 400, like the devices 10, 200 and 300 discussed above in relation to FIGS. 1-4, 5-7, and 19, is again suitable for use and sized for placement/to fit at a selected location (e.g., supravalvular) within the heart. As outlined above, the suitable location may be either of two different cardiac arteries. As with the embodiments discussed above, the device 400 again may also prove suitable for use elsewhere in the vasculature.

Figure 20:
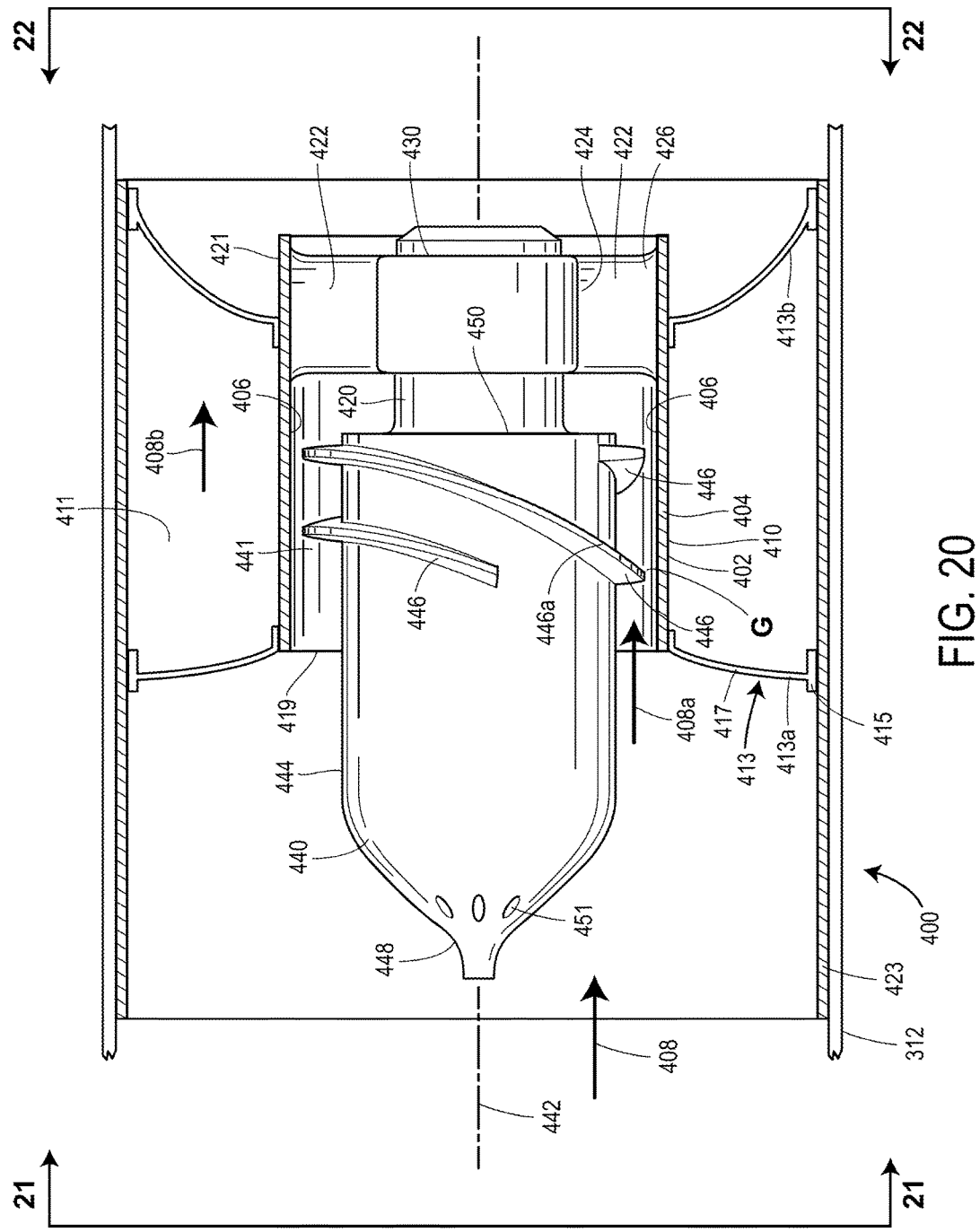
FIG. 20 is an enlarged elevational view, partly in section, of a further exemplary form for an assist device including a rotor and stator disposed within a flow housing and assembled in accordance with the teaching of the present invention.

Referring to FIG. 20, the device 400 includes a shroud or flow housing 402, and the flow housing 402 includes a cylindrical wall 404 with an inner surface 406 and an outer surface 410. The flow housing 402 is sized and configured to be disposed within the blood vessel 312 (visible in FIG. 20 and only partially visible in FIG. 21), such as a cardiac artery, as mentioned previously. In the example shown, the flow housing 402 again is sized to define an annular space 411 between the outer surface 410 of the flow housing 402 and the surrounding blood vessel 312.

Once again the flow housing 402 is supported and/or otherwise secured in place within the blood vessel 312 by a support assembly 413, which operatively couples the flow housing 402 to the surrounding blood vessel 312. Again the support assembly 413 includes one or more landing area portions 415 arranged to make contact with the surrounding blood vessel 312, and a plurality of connectors 417 that connect the flow housing 402 to the landing area portions 415. Again the support assembly 413 includes an upstream or first portion 413a which attaches to the flow housing 402 generally adjacent to a forward portion 419 of the flow housing 402, and further includes a downstream or second portion 413b which attaches to the flow housing 402 generally adjacent to a rearward portion 421 of the flow housing 402. Still other arrangements for supporting the flow housing 402 within the blood vessel 412 may prove suitable. The support assembly 413 may be pre-formed at a desired size, or may be expanded in place using conventional materials and methods.

Figure 21:
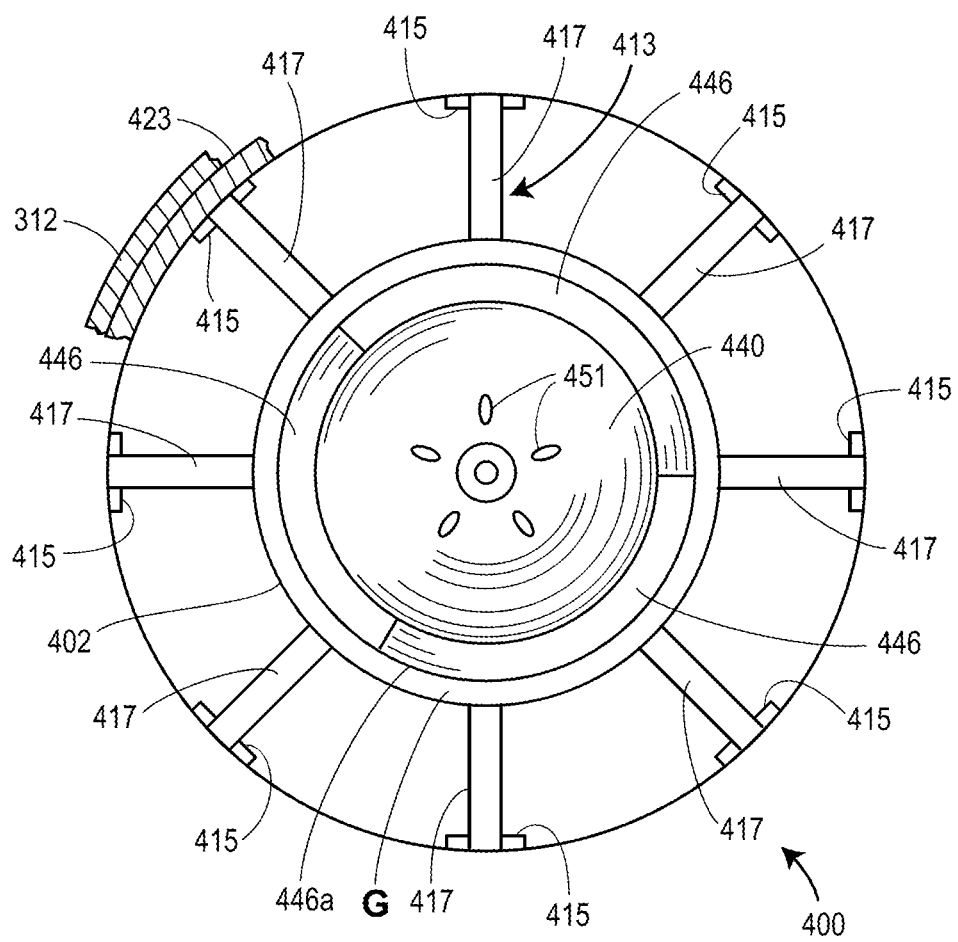
FIG. 21 is a front or upstream side elevational view of the assist device taken along line 21-21 of FIG. 20.

As shown in FIGS. 20 and 21, the landing areas 415 of the support assembly 413 may be suitably secured to the blood vessel 312 using any suitable means. Alternatively, the landing areas 415 of the support assembly 413 may be suitably secured to a vascular graft 423 (visible in FIG. 20 and only partially visible in FIG. 21), which may be a Dacron graft or any other suitable vascular graft. With the use of the vascular graft 423, the device 400 may be placed as a unit at the desired location in the blood vessel 412 using any suitable delivery technique, such as a trans-apical approach. In turn, the vascular graft 423 may be suitably secured to the surrounding blood vessel 312 using other conventional techniques.

Referring to FIG. 20, the device 400 includes a stator 420 which may be the same or similar to the stators 220 and 320 discussed above. Again the stator 420 of the device 400 is disposed inside of the flow housing 402 and includes a plurality of support struts 422 each having a first end 424 connected to the stator 420 and a second end 426 disposed against the inner surface 406 of the flow housing 402. As with the device of FIGS. 5-7, the stator 420 has an upstream end 428 (obscured in FIG. 20 but visible in FIG. 24 and partially in FIG. 25), and a downstream end 430. Although only two (2) support struts 422 are visible in FIGS. 20 and 24, additional support struts may be provided, such as the number of support struts visible in, for example, FIG. 22. Again the support struts 422 are preferably disposed equidistant about the stator 420, although other arrangements may prove suitable.

As with the prior embodiments, the device 400 further includes a rotor 440. The rotor 440 may be similar in many respects to the rotors outlined above with respect to the above-described embodiments, and again is sized for placement within the flow housing 402 in such a fashion that the rotor 440 can rotate about its axis 442. In the example shown, the flow housing 402 and the rotor 440 are sized to define an annular space 441 between the rotor 440 and the inner surface 406 of the flow housing 402, and the device 400 again defines a flow path 408 extending generally through the device 400. In the example shown, a first portion 408a of the flow path 408 extends through the flow housing 402 via the annular space 441 between the rotor 440 and the flow housing 402, and a second portion 408b of the flow path 408 extends around the flow housing 402 via the annular space 411 between the flow housing 402 and the surrounding blood vessel 312.

The rotor 440 has an outer surface 444 facing the inner surface 406 of the wall 404 of the flow housing 402, and the rotor 440 includes at least one blade (or other suitable flighting) 446, again with the blade 446 angled with respect to the flow path 308. The rotor 440 has an upstream end 448 and a downstream end 450. In the example of FIG. 20, the rotor 440 protrudes from the flow housing 402, and the blade(s) 446 are disposed generally toward the rearward end 450. Preferably, an outer end 446a of the blade 446 is spaced slightly from the inner surface 406 of the flow housing 492, leaving a small gap G. The gap G is best visible in FIGS. 20 and 21. The forward end 448 of the rotor 440 preferably includes apertures 451 which, in one exemplary form, allow a limited amount of blood to flow through the apertures.

The rotor 440 is again rotatably mounted to the stator 420 using first and second bearings 460 and 462, which may be the same or similar to the bearings discussed above with respect to the prior embodiments.

As with the prior embodiment, the first bearing 360 may be a mechanical pivot. Alternatively, the first bearing 360 may be a hydrodynamic pivot. Further, the first bearing 360 may be a magnetic bearing, such as is described above relative to the prior embodiments. Still other alternatives are possible according to the teachings of the disclosed example of the present invention. As with the above-described examples, the rotor 440 includes a field magnet, which may be in the form of a permanent magnet, similar to the magnets discussed in the above embodiments, and includes windings, which also may be in the form of the windings or coils discussed above with respect to the prior embodiments. In response to the application of electrical power from the power source to the windings, the windings interact with the magnet, causing the rotor 440 to rotate about its axis 442 within the flow housing 402 as in the manner discussed with respect to the prior embodiments.

FIGS. 22 and 23 illustrate additional aspects of the support struts 422. The support struts 422 include a leadings edge 445 and a trailing edge 447. The struts 422 may be angled with respect to the axis 442 of the device 400. The struts may have a constant angle, or the struts 422 may have a curved or variable angle. Other arrangements may prove suitable. In the disclosed example, the struts 422 having an angle may influence the direction of flow as the blood comes off the blades 446 on the rotor 440 as shown in FIG. 23, thus altering the direction as illustrated by the exemplary progression of flow arrows 471, 473 and 475.

Figure 24:
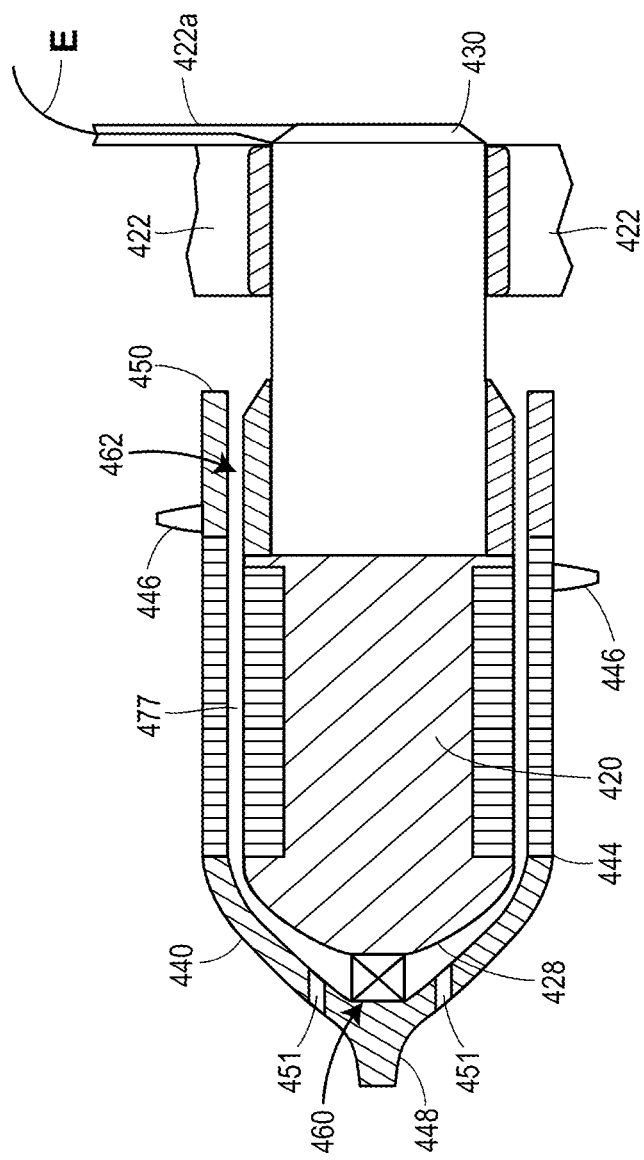
FIG. 24 is a fragmentary view, partly in section, illustrating exemplary aspects of the rotor and the housing, including integrating portions of the power cord or cords or other suitable electrical coupling into one of the support struts.

FIG. 24 illustrates the cross-section of the rotor 440 mounted to the stator 420 with the bearing 460 and the bearing 462. An annular gap 477 is defined between the rotor 440 and the stator 420. The apertures 451 allow limited flow communication between the gap 477 and the areas both in front of and behind the device 400. The example of FIG. 24 also shows an exemplary form of incorporating the electrical coupling or power cord E into a portion 422a of one of the support struts 422. Using such an arrangement, effects of the power cord E on blood flow can be minimized. Further, the portion 422a may be suitably extended through the support assembly 413 to a convenient point to exit the blood vessel, again to minimize the effect on blood flow.

Figure 26:
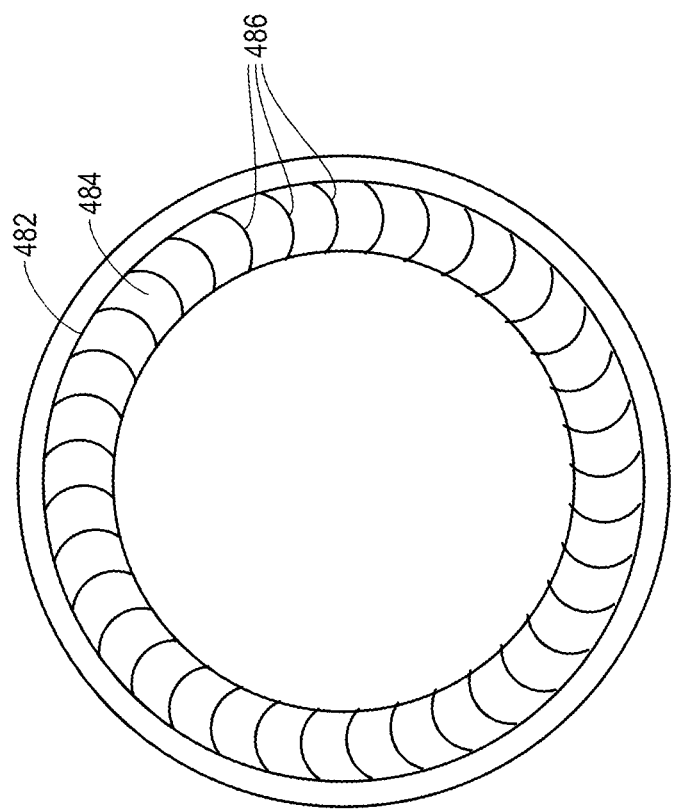
FIG. 26 is an enlarged plan view of an exemplary grooved bearing race for use with the exemplary bearing of FIG. 25.
Figure 25:
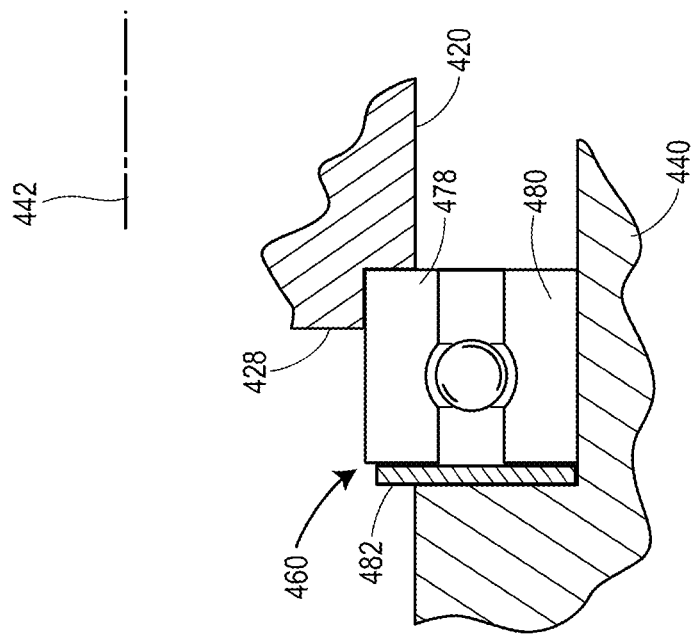
FIG. 25 is an enlarged cross-sectional view of one exemplary bearing assembly for rotationally coupling the upstream portion of the rotor to the stator.
Figure 27:
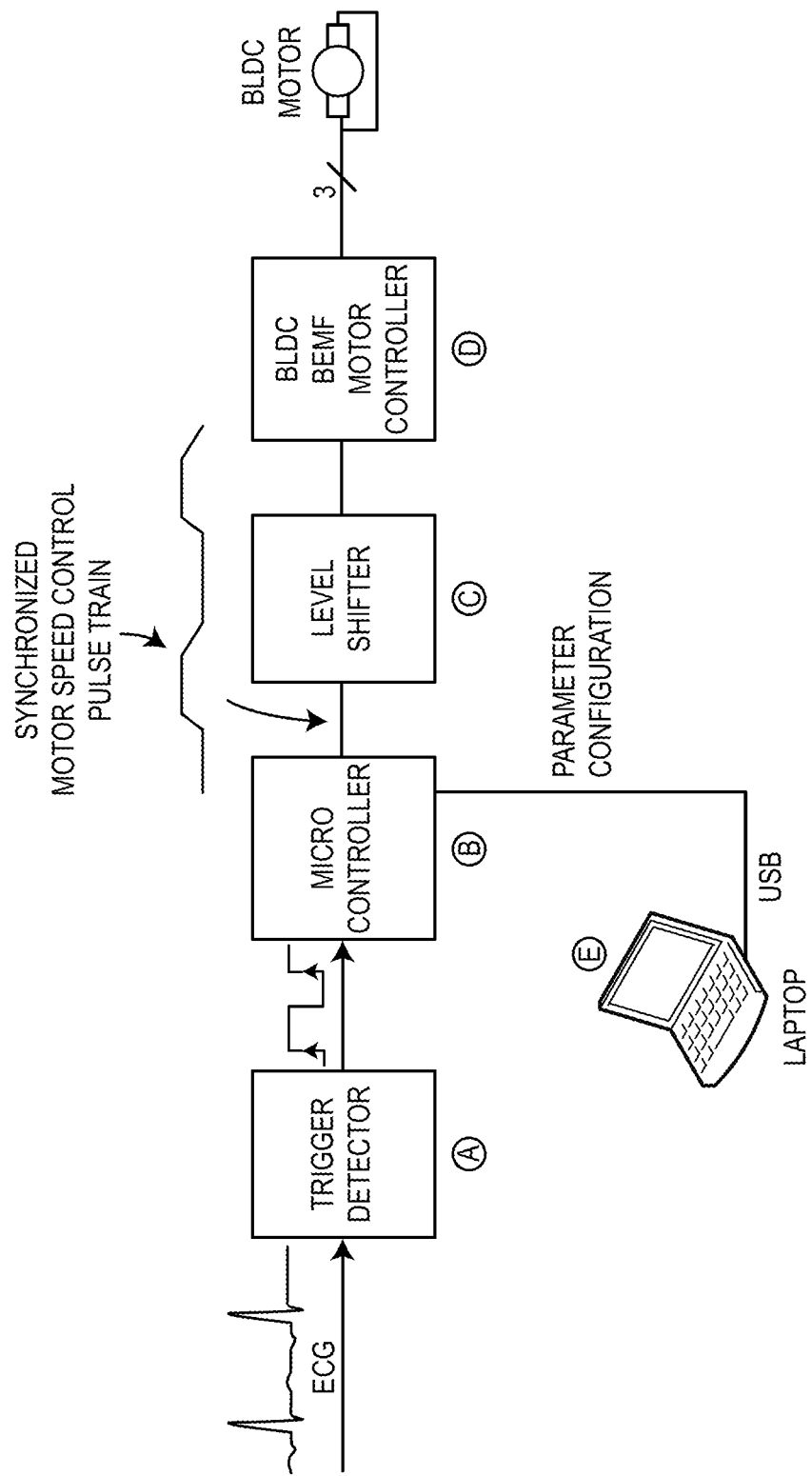
FIG. 27 is a block diagram of an exemplary control loop for controlling the assist device.

FIG. 25 shoes one exemplary form for the bearing 460. The bearing 460 includes a first race 478 mounted to the forward end 428 of the stator 420, and further includes a second race 480 mounted to an interior portion of the rotor 440. A washer or disc 482 surrounds the bearing 460. The disc 482 may function to hold back pressure external to the device 400, and may serve to minimize thrombus. As shown in FIG. 26, a face 484 of the disc 482 may include grooves 486, which may be cut or etched into the face 484 of the disc 482.

In one or more of the illustrated examples, the flow housing may be sized to be approximately 20 mm, while the blood vessel may typically measure approximately 30-40 mm.

The discussion of the devices 10 and 200 is applicable with equal force to the devices 300 and 400 as it relates to the operation of the associated power source 280 and controller 282.

One or more of the teachings applicable to the embodiments of FIGS. 1-4 and/or 5-7 may also be applied to the embodiment of FIG. 19, and to the embodiment of FIGS. 20-26. Upon reading the present disclosure, one of skill in the relevant art also may combine and/or substitute aspects of the devices 10, 200, 300, and/or 400 as desired.

Having thus described the structure and operation of the above-described devices 10, 200, 300 and 400, exemplary forms and/or methods of placement is now discussed. While much of the discussion relates to one of the devices, it will be recognized that the discussion applies with equal force to the remaining embodiments.

Figure 8:
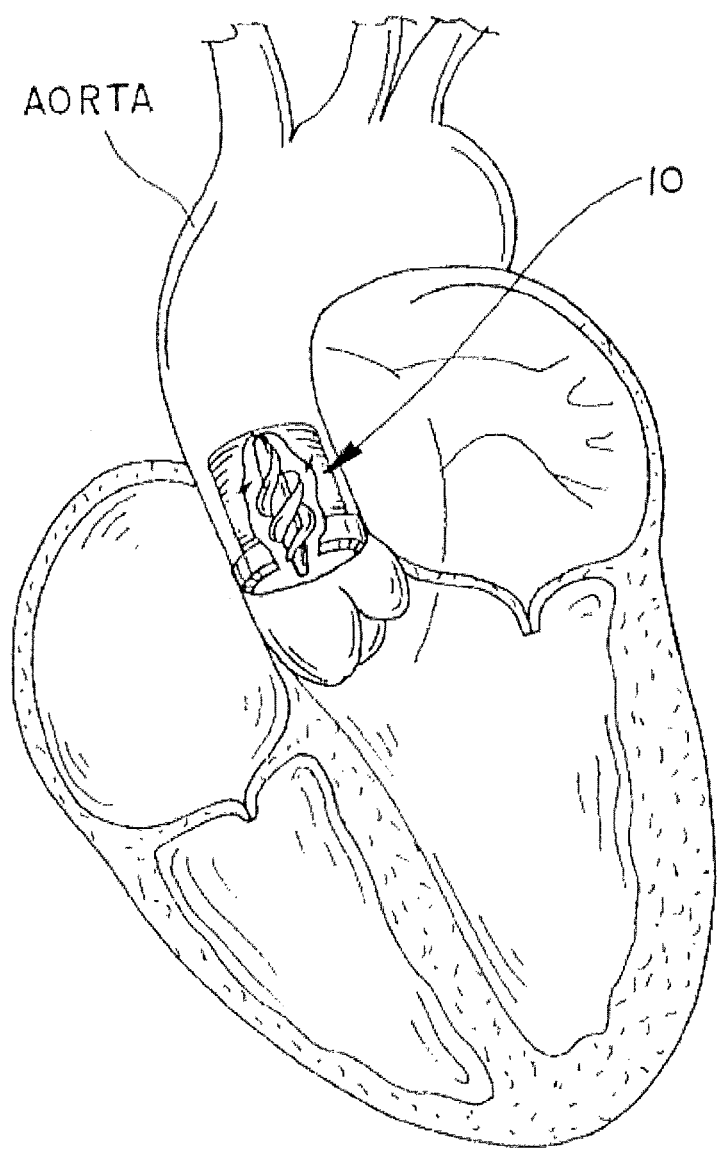
FIG. 8 is an enlarged elevational diagrammatic illustration of the heart, partly in section, and illustrating a device assembled in accordance with the teachings of the disclosed invention in place at a selected location on the aorta to function as a left ventricular assist device.
Figure 9:
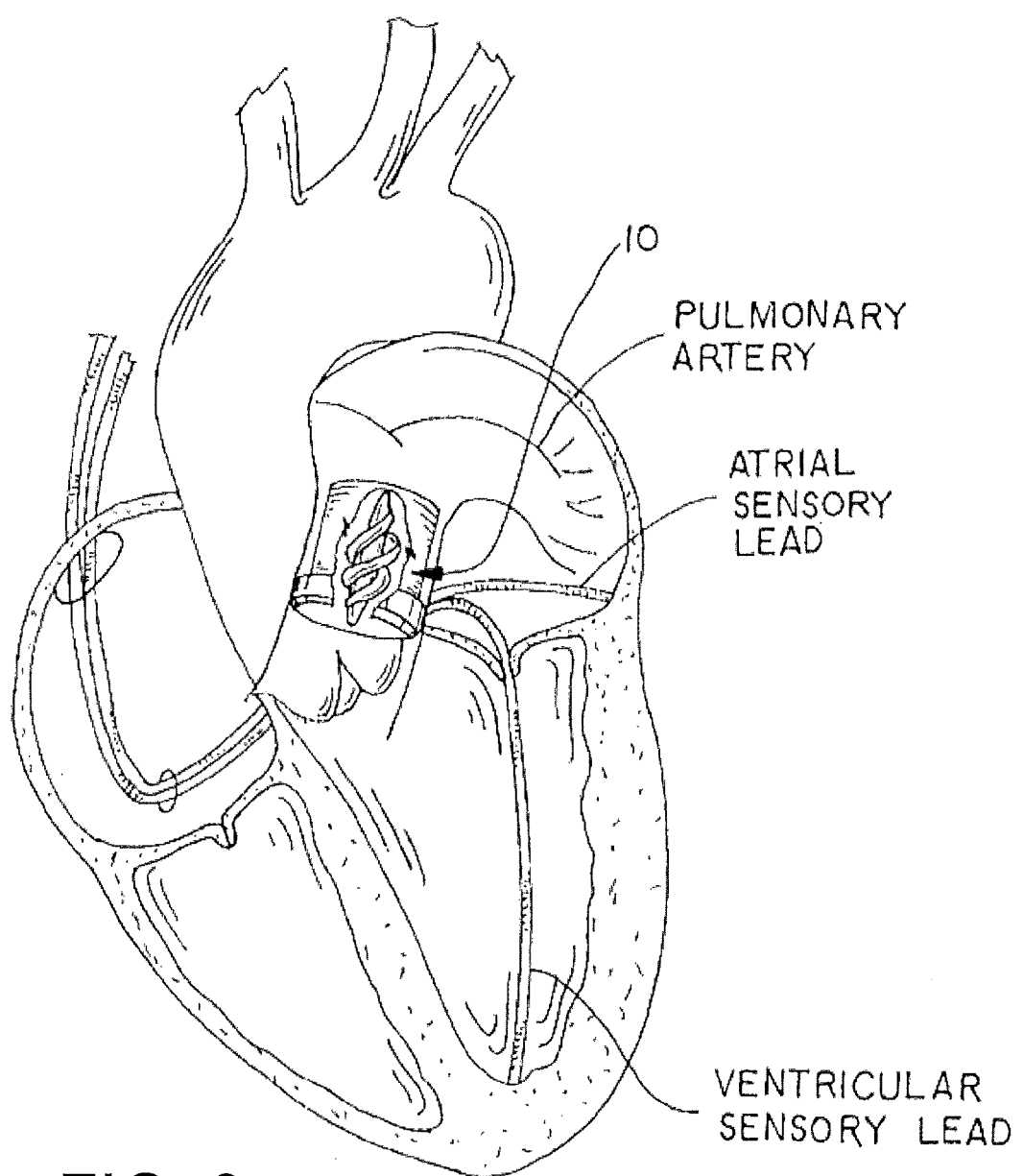
FIG. 9 is another enlarged elevational diagrammatic illustration of the heart, partly in section, and a device assembled in accordance with the teachings of the disclosed invention in place at a selected location on the pulmonary artery to function as a right ventricular assist device.

Referring now to FIG. 8, the device 10 is shown disposed about the aorta in a supravalvular position in order to assist with left ventricular failure. On the other hand, and referring to FIG. 9, the device 10 is shown disposed about the pulmonary artery, again in a supravalvular position, in order to assist with right ventricular failure. The device 10 may prove suitable for still other selected locations. Those of skill in the art, upon reading the present disclosure, will understand that the teachings of FIGS. 8 and 9 may be combined, thus creating a bi-ventricular assist device by placing the device 10 in the aorta as shown in FIG. 8, and by placing another device in the pulmonary artery as shown in FIG. 9. The device 10 shown in each of FIGS. 8 and 9 may incorporate either the rotor 16 of FIGS. 2 and 3, or may incorporate the rotor 116 of FIG. 4. Alternatively, the device 200 may be used.

Figure 10:
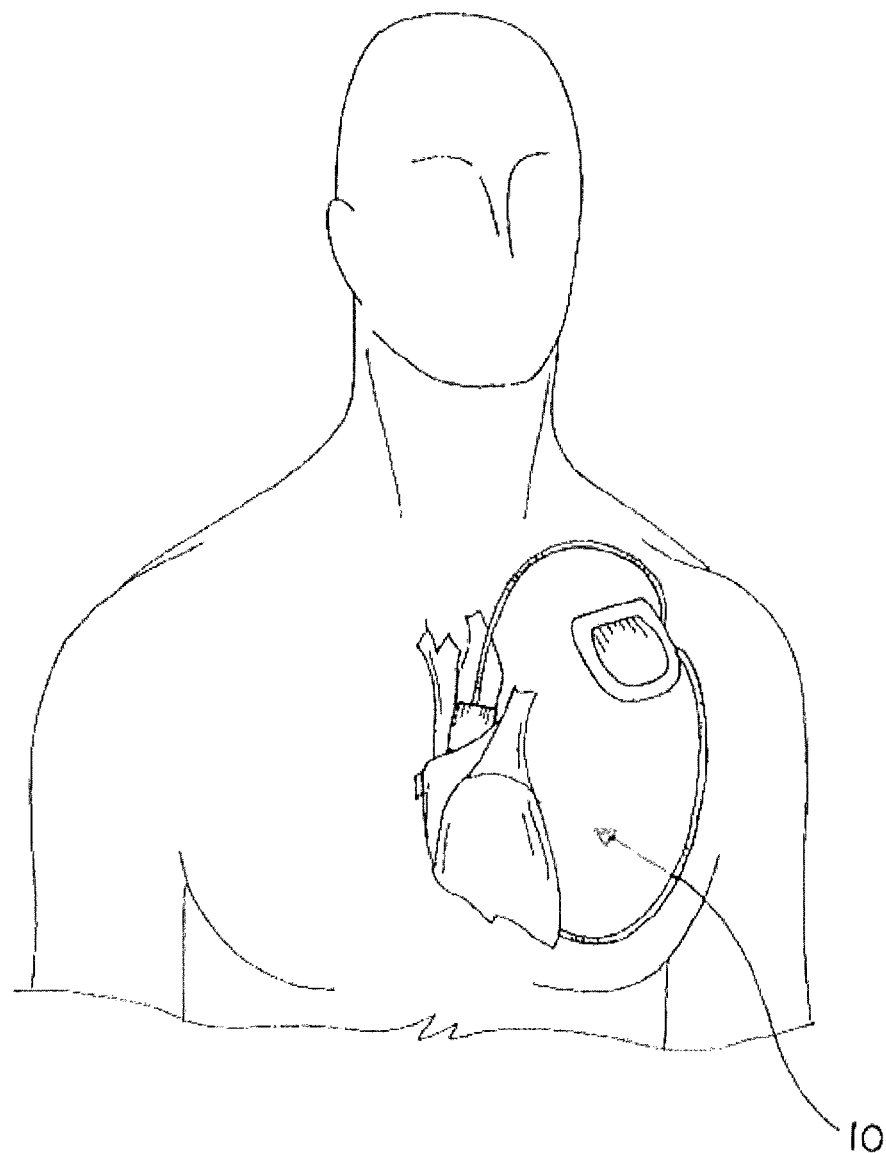
FIG. 10 is a view of the disclosed device implanted in a patient and operatively coupled to an implantable unit including a power source and a timing control module.

Referring now to FIG. 10, the device 10 is shown implanted within the body and coupled to the power source 32 and the timing control module 34 by one or more suitable links, with the power source 32 and the timing control module 34 incorporated into a single, implantable unit.

Figure 11:
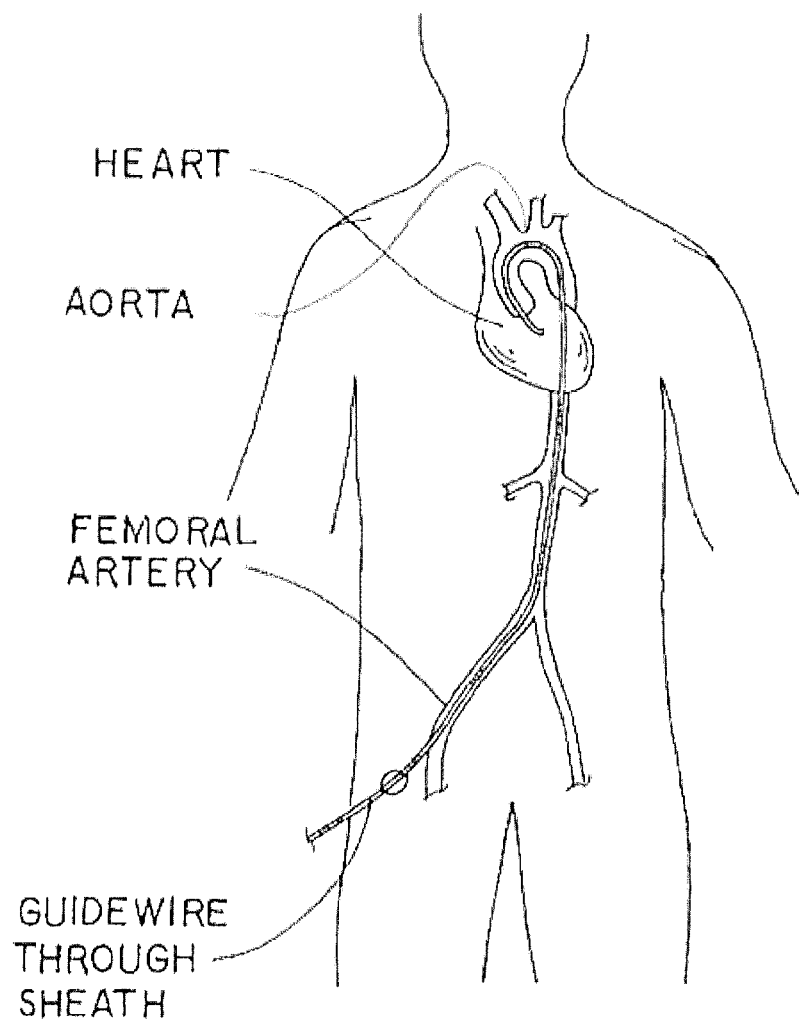
FIGS. 11-14 are schematic illustration of one exemplary method of percutaneous placement of portions of the disclosed device at the selected location.
Figure 12:
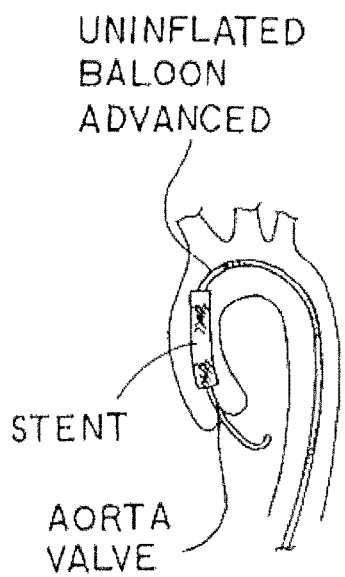
Figure 13:
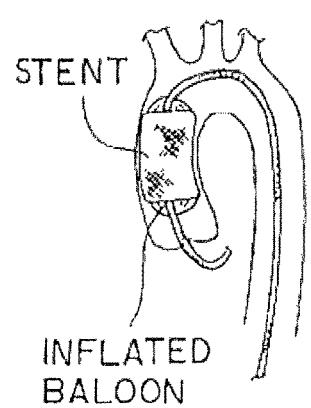
Figure 14:
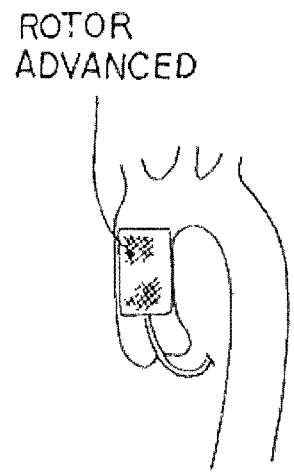
Figure 15:
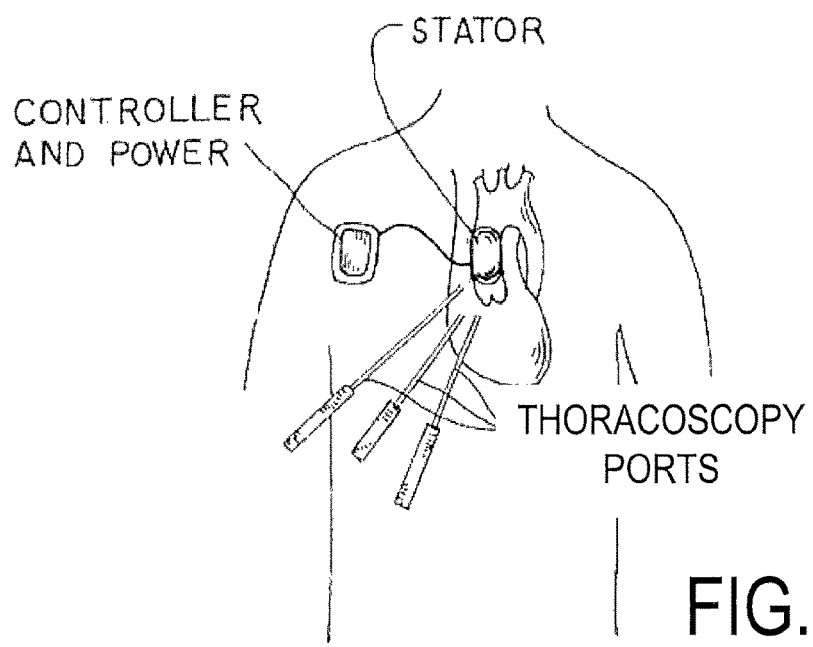
FIG. 15 is another schematic illustration illustrating additional aspects of exemplary methods for placement of the disclosed device at the selected location.

Referring now to FIGS. 11-15, an exemplary percutaneous placement method is illustrated. FIG. 11 illustrates percutaneous access to the desired location, in this case the aorta, via the femoral artery. Initially, the stent 12, in a collapsed configuration, is placed at the desired location above the aortic valve using a suitable guide wire and suitable known techniques as shown in FIG. 12. As shown in FIG. 13, the stent 12 is expanded from the collapsed configuration of FIG. 12 to an expanded configuration using an inflatable balloon and known techniques. In the expandable configuration of FIG. 13, stent 12 now defines the suitable flow path 14. Next, as shown in FIG. 14, the rotor 16 is advanced to the desired location within the stent 12, again using a suitable guide wire and known techniques. The rotor 16 may be expanded from a collapsed configuration during delivery to an expanded configuration by, for example, removing a sheath, or by using other suitable expansion techniques. The collar 26, as well as the power source 32, the timing control module 34, and the sensor 66 along with all suitable links, may be implanted using conventional techniques such as thoracoscopy, as illustrated in FIG. 15, or other suitable techniques.

Figure 17:
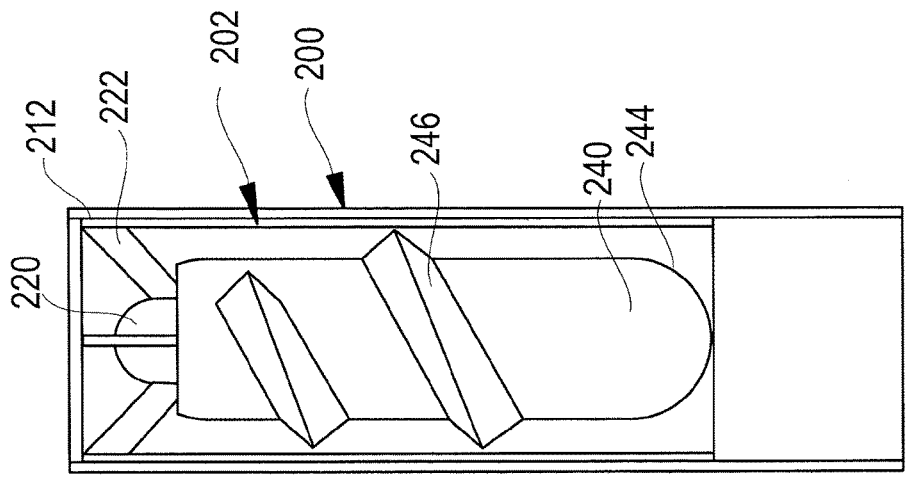
FIG. 17 is an enlarged fragmentary elevation view, partly in section, and illustrating the device according to FIGS. 5-7 as it is secured to the already expanded stent.
Figure 16:
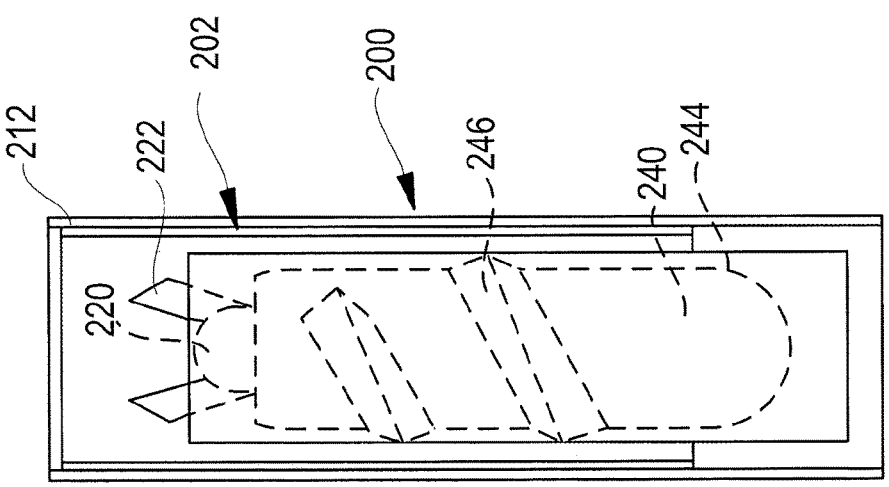
FIG. 16 is an enlarged fragmentary elevation view, partly in section, and illustrating one exemplary method of the device according to FIGS. 5-7 as it is introduced into the already expanded stent.

In a similar fashion, the placement of the device 200 is illustrated in FIGS. 16 and 17. In particular, as illustrated in FIG. 16, the stent 202 may be selected and placed at the selected location using known techniques in a collapsed configuration and then expanded from a collapsed configuration to an expanded configuration also using known techniques (e.g., through the use of an inflatable balloon). As is also illustrated in FIG. 16, the combination of the stator 220 and the rotor 240 may be placed in an introducer jacket, which jacket collapses the blades 246 against the rotor 240. The support struts 222 may also be folded or otherwise collapsed against the stator 220. The introducer jacket is then introduced into the stent 202, and once the struts 222 are in place, the jacket may be removed. For example, the removal of the jacket may cause the blades to extend from the outer surface 244 of the rotor 240, and places the device 200 in condition for use, as illustrated in FIG. 17. The power source 280, the controller 282, and the sensor 288, along with all suitable links, may be implanted using conventional techniques such as thoracoscopy, as is illustrated in FIG. 15 relative to device 10, or other suitable techniques and operatively coupled to the device 200 (e.g., the power source 280 to windings of the stator 220).

When assembled in accordance with an exemplary aspect of the invention, when the device is used for left ventricular support the device may be placed above the aortic valve and above the origins of the coronary arteries (for example, approximately 1 cm superior to the level of the sino-tubular junction). In such an application, coronary perfusion would not be affected.

The device may be placed through the 2nd right intercostal space through an anterior mini-thoracotomy, off-pump, or through an upper hemi-sternotomy or traditional median sternotomy. Preferably, one or more of the collar, the stent, and the rotor may be collapsible, and thus suitable for minimally invasive placement at the selected location(s). One exemplary a cardiac surgical approach would be a hybrid operating room with the placement of the impeller and stent percutaneously. Following a median sternotomy or upper hemisternotomy, once the aorta has been cross-clamped and the patient placed on cardiopulmonary bypass, the aorta could need to be incised. The decision whether to remove the native aortic valve would be based on its integrity and condition. The device would be mounted above the origins of the coronary arteries. The power source to the unit may be epi-aortic and would be threaded through subcutaneously to the location of the power pack. The device may be mounted on a titanium, or other suitable material, mesh stent-like structure, which would be lightweight and extremely strong. The device mechanism would be mounted within that mesh which would be sized appropriately to fit the aorta. In the case of pulmonary location, this would need to be placed in the supravalvular position in the pulmonary artery.

Figure 18:
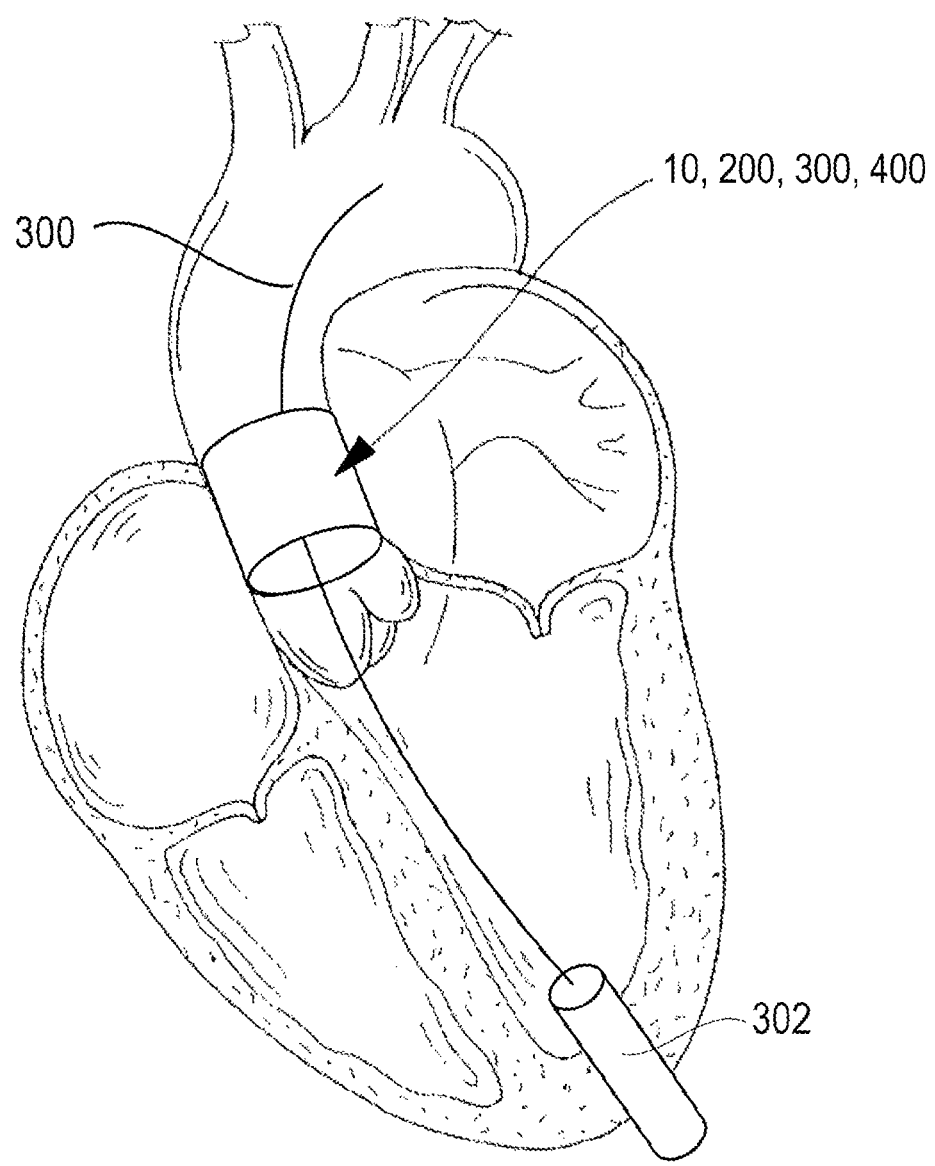
FIG. 18 is an enlarged elevational diagrammatic illustration of the heart, partly section, and illustrating a device assembled in accordance with the teachings of the disclosed invention in place at a selected location on the aorta to function as a left ventricular assist device, as well as a delivery catheter and guide wire used to place the device through a trans-apical route.

In another exemplary form, the device (whether the device 10 or the device 200) may be placed using a trans-apical approach as illustrated in FIG. 18. The feasibility of the trans-apical approach is well described relative to its use for trans-apically delivered aortic valves. According to such an embodiment, the aorta would not need to be incised, as the device would be inserted through the left ventricular apex via a mini-thoracotomy (left anterolateral incision, through the fifth or sixth intercostal space). In particular, a delivery catheter or guide wire 300 is introduced directly into the left ventricle using the mini-thoracotomy, and the catheter or guide wire 300 initially traverses the aortic valve under the guidance of trans-esophageal echocardiography and fluoroscopy to the appropriate position (e.g., above the origin of the coronary arteries). A sheath 302 may also be delivered to the left ventricular apex to maintain intraventricular access. The device 10, 200 may then be delivered through the sheath 302 over the catheter or guide wire 300 into place, first the stent and then the remainder of the device (the rotor or the rotor/stator combination, as collapsed within the introducer jacket, e.g.). This approach would minimize the risk of systemic embolization from a calcified aorta and would also avoid exposing the arterial circulation in candidates at risk of arterial compromise from embolization.

The exemplary device of FIGS. 1-4 includes the rotor or impeller on a magnetic mount, such that the rotor is therefore magnetically suspended or levitated as outlined above. As mentioned above relative to the exemplary devices of FIGS. 1-7, the impeller preferably includes a collapsible pumping surface or structure, such as collapsible blades or other suitable surface, which allow for percutaneous as well as trans-apical placement. The impeller may, in effect, function as a "suction" type of system. With each systolic contraction of the heart, the programming within the pacemaker-like timing control module or unit would activate the pumping action of the device. The rotor would speed up from its low baseline speed to a higher speed based on requirement, thus creating a negative vortex below it which would augment natural contractility of the heart as blood exits through the aorta and through the device. With diastole, the device would slow down or even stop. Keeping the rotor moving may be beneficial from a power conservation standpoint. Also, the stopped or very slowly moving rotor preferably functions in a valve-like capacity to prevent backflow of blood through the aorta or pulmonary artery and back into the ventricle. With the next cycle, the procedure would be repeated. The same method of installation and placement of the power source would be employed in the pulmonary position for right ventricular augmentation.

Preferably, the timing of the pump function would be optimized to provide phasic flow which would be coordinated with ventricular systole. In many patients with end-stage heart failure, a dual chamber or bi-ventricular pacemaker is often used to create synchronicity in contraction between the atrial and ventricular chambers. Placement of this device would not alter such function. The sensor 68 (or 288) includes electrodes which would be placed on the heart to obtain atrial and ventricular electrograms (the native cardiac rhythms) and this data would be sent to the timing control module 34 (or controller 282). The power source 32 (or 280) preferably is a pacemaker-like power source. The pumping function of the device 10 (or 200) would be timed to coordinate with the ventricular electrical impulse indicating the onset of systole. A pressure sensor may also be provided and preferably would be available to detect changes in pressure thus providing additional information. In this way, the device 10 would be able to adapt to changing needs and changing heart rate conditions. This would result in augmentation of blood flow in a more synchronous fashion. The timing control module 34 would also have algorithms incorporated to take into account the timing of atrial and ventricular signals and input of pressure sensor data to indicate when pressure is rising, thus improving the timing of augmentation of phasic flow. In effect, the pump would increase its flow based on physiologic need. The mechanism is that the baseline speed of the impeller increases, thus forcing blood across the device at higher velocity and augmenting native cardiac function.

Additionally, there are several possibilities to prevent thrombus formation. In one iteration, systemic anticoagulation with traditional anticoagulants in the form of warfarin or low molecular weight heparin could be used with use of low dose aspirin as an anti-platelet agent. In another iteration, the device could be coated with material that prevents formation of thrombus. A non-thrombogenic surface would therefore minimize the need for systemic anticoagulation. In another potential iteration, the use of a direct current charge on the device by coating it with a dielectric and using a specific circuit to distribute the charge could be used (such as that found in PCT Publication No. WO 2008/024714 A1). In another iteration the system could be coated with fibrinogen like peptide that would prevent thrombus formation and prevent the need for systemic anticoagulation.

The unit including the power source 32 and the timing control module 34 (or power source 280 and controller 282) preferably would be positioned as illustrated in FIG. 9. In one preferred form, the power source would be placed in the infra-clavicular or sub diaphragmatic regions with subcutaneous wires to the device for power delivery as well as control of the device. The facility for near frequency communication (NFC) with the power source and control unit, via means of a cellular device (iphone, android device, blackberry RIM or "smart phone") would be built into the system thus providing a means of wireless programming. The NFC control unit, which the patient would carry would also provide a constant monitoring system providing information on power settings, cardiac output and display any potential problems which need to be addressed; default safety algorithms will be deployed and real-time data alerts will be sent to the on-call cardiology and cardiovascular team responsible for the patient from their home setting. The power source preferably would be transcutaneously charged. Therefore, the entire system would be completely implantable, with no external leads or wires. Still preferably, wireless cell phone technology or other suitable wireless communication protocols may be used, enabling the relevant health care providers to continuously monitor data from the cloud.

The device as described functions in a synchronous fashion to augment cardiac contractility. Therefore if cardiac standstill occurs, or ventricular arrhythmias occur which prevent normal electrical activation, problems with device function could occur. One iteration of the device includes the use of a defibrillator lead which is attached to the power pack which can be used to sense the presence of ventricular arrhythmias and deliver an appropriate shock to the heart to terminate the arrhythmia. This would be necessary in order to provide continued cardiac output. This could be incorporated into the algorithms which would be programmed into the device. Atrial arrhythmias should not be as much of a problem, provided ventricular rate is maintained.

Because of the supravalvular nature of the device and its lack of interference with native cardiac function, it could be used in different cardiac failure states. In pure left ventricular failure, the valve would be placed in the supra-aortic position. In pure right ventricular failure, it would be placed in the supra-pulmonary valve position. In biventricular failure, two devices could be employed sitting in the aorta and the pulmonary artery with appropriate power packs for each functioning device. The power packs could be placed in a infra-clavicular of infra-diaphragmatic location. In pulmonary hypertension with severe right heart failure, the device could be used in the supra-pulmonary valve position augmenting the function of the failing right ventricle. By virtue of its location, the etiology of the heart failure becomes less important. Thus, it could also be used in diastolic dysfunction and restrictive cardiomyopathic states. By simply augmenting device function and increasing the revolutions per minute during phasic contraction of the heart, the timing of diastolic filling becomes less important.

Because of its location, the device would function adequately as a heart valve in addition to being an assist device. Hence, the native valves could be removed and the ability to stop or slow down the impeller completely would prevent backflow of blood and minimize forward flow of blood during the diastolic phase.

Because of its ability to be located in any major vessel, the device could also be used as a peripheral circulatory assist device for severe peripheral vascular disease. In that iteration, it could be placed in the descending aorta or in the femoral or iliac vessels and thus augment blood flow to the lower limbs. Similarly, it could be placed in other locations within the aorta to augment blood flow in the relevant vascular beds. For instance, in individuals with severe peripheral vascular disease, placement of the device in the infra-renal position would augment natural blood flow and increase perfusion of the lower limbs. In critical lower limb ischemia, improvement of a proximal blood flow may allow the ability to treat the lower limb ischemia.

The disclosed device and/or method may additionally prove especially useful or suitable for placement during congenital heart surgery in patients requiring hypoplastic left heart reconstruction. Those of skill in the art, upon reading the present disclosure, will also find the disclosed device and/or method useful in other procedures as well.

The disclosed device and/or method may also prove especially adaptable for certain energy saving or energy providing technology. For example, the device may be adapted to extract and/or use kinetic energy from the heart and/or from the flow of blood, and use that energy to supply at least a portion of the power requirements of the device. Further, the device may be especially suitable for use with bionic fuel cell power, which can extract electrons from blood glucose, thus supplying power to the device. A more detailed explanation of such bionic fuel cell technology can be found in *Microfabricated Miniature Biofuel Cells with Nanoengineered Enzyme Electrodes*, by Nishizawa et al. and *Miniaturized Microfluidic Biofuel Cells*, by Nishizawa.

Preferred embodiments of this invention are described herein, including the best mode or modes known to the inventors for carrying out the invention. Although numerous examples are shown and described herein, those of skill in the art will readily understand that details of the various embodiments need not be mutually exclusive. Instead, those of skill in the art upon reading the teachings herein should be able to combine one or more features of one embodiment with one or more features of the remaining embodiments. Further, it also should be understood that the illustrated embodiments are exemplary only, and should not be taken as limiting the scope of the invention. All methods described herein can be performed in any suitable order unless otherwise indicated herein or otherwise clearly contradicted by context. The use of any and all examples, or exemplary language (e.g., "such as") provided herein, is intended merely to better illuminate the aspects of the exemplary embodiment or embodiments of the invention, and do not pose a limitation on the scope of the invention. No language in the specification should be construed as indicating any non-claimed element as essential to the practice of the invention.

What is claimed is:

1. A ventricular assist device for a human heart comprising:
    a flow housing having a generally cylindrical wall with an inner surface defining a portion of a flow path, the flow housing having an outer surface and sized for placement within a blood vessel;
    a stator disposable within the flow housing, the stator having a plurality of support struts operatively coupling the stator to the flow housing;
    a rotor including an outer surface facing the inner surface of the cylindrical wall of the flow housing, the rotor rotatably coupled to the stator and rotatable with respect to the stator about a rotational axis, the rotor defined in part by at least one blade angled with respect to the rotational axis;
    one of the rotor and the stator comprising a field magnet and the other of the rotor and the stator comprising windings;
    a power source operatively coupled to the windings;
    a controller operatively coupled to the power source to selectively control the power source to vary the rotational speed of the rotor; and
    a vascular graft surrounding the flow housing and coupled to the flow housing, the vascular graft sized for placement within the blood vessel and arranged for coupling to the blood vessel.

2. The device of claim 1, including an annular space defined between the outer surface of the flow housing and the vascular graft, wherein the annular space defines a portion of a second flow path.

3. The device of claim 1, wherein the vascular graft is coupled to the flow housing by a plurality of supports or by a mesh support; or the cylindrical stent wall comprises a metal mesh tube.

4. The device of claim 1, wherein the rotor comprises the field magnet and the stator comprises the windings, the windings operatively coupled to the power source, and wherein the stator has an upstream end and a downstream end, the plurality of support struts depending from adjacent the downstream end of the stator connected to the inner surface of the flow housing.

5. The device of claim 1, further comprising at least first and second bearings disposed between the stator and the rotor to rotatably mount the rotor on the stator, the first bearing disposed adjacent an upstream end of the rotor and the stator and the second bearing disposed adjacent a downstream end of the rotor and the stator, wherein the first bearing is a mechanical pivot and the second bearing is a magnetic bearing and comprises first and second magnets, the first magnets attached to the rotor and the second magnets attached to the stator, the first and second magnets having aligned polarities.

6. The device of claim 5, wherein the first bearing is a hydrodynamic pivot and the second bearing is a magnetic bearing and comprises first and second magnets, the first magnets attached to the rotor and the second magnets attached to the stator, the first and second magnets having aligned polarities.

7. The device of claim 1, wherein the at least one blade has one of a constant pitch or a variable pitch.

8. The device of claim 1, wherein the controller is programmed to one of: (1) operate the power source to provide a pulsatile flow; or (2) control the rotational speed of the rotor between a baseline speed and a higher speed.

9. The device of claim 1, further comprising a cardiac sensor operatively coupled to the controller, the controller being programmed to use the cardiac sensor to determine native cardiac rhythms, and to control the rotational speed of the rotor in response to the native cardiac rhythms.

10. The device of claim 1, wherein the stent, rotor and stator are sized to fit within one of the aorta and the pulmonary artery or within one of the aorta and the pulmonary artery at a selected location that is supravalvular; or wherein one or more of the stent, the stator and the rotor are coated with an anti-coagulant.

11. The device of claim 1, wherein the power source and the controller are sized for subcutaneous placement; or wherein the power source is arranged for transcutaneous charging; or wherein the controller is arranged for transcutaneous programming.

* * * * *